US010507293B2

(12) United States Patent
Goodman et al.

(10) Patent No.: US 10,507,293 B2
(45) Date of Patent: Dec. 17, 2019

(54) HEMOSTATIC POWDER DELIVERY DEVICES AND METHODS

(71) Applicant: Ethicon, Inc., Somerville, NJ (US)

(72) Inventors: John Goodman, Ann Arbor, MI (US); Alex W. Kiturkes, Bridgewater, NJ (US); Jared Schneider, Raritan, NJ (US)

(73) Assignee: Ethicon, Inc., Somerville, NJ (US)

( * ) Notice: Subject to any disclaimer, the term of this patent is extended or adjusted under 35 U.S.C. 154(b) by 268 days.

(21) Appl. No.: 15/092,712

(22) Filed: Apr. 7, 2016

(65) Prior Publication Data

US 2016/0375202 A1    Dec. 29, 2016

Related U.S. Application Data

(60) Provisional application No. 62/183,916, filed on Jun. 24, 2015.

(51) Int. Cl.
*A61M 11/00* (2006.01)
*A61M 13/00* (2006.01)
*A61B 17/34* (2006.01)
*A61L 26/00* (2006.01)
*A61M 35/00* (2006.01)

(52) U.S. Cl.
CPC ....... *A61M 11/003* (2014.02); *A61B 17/3423* (2013.01); *A61L 26/009* (2013.01);
(Continued)

(58) Field of Classification Search
CPC ........ A61M 2205/10; A61M 2205/073; A61M 2205/071; A61M 11/003; A61M 11/006;
(Continued)

(56) References Cited

U.S. PATENT DOCUMENTS 5,740,792 A    4/1998  Ashley et al.
6,866,039 B1 *  3/2005  Wright .............. A61M 15/0041
                                                    128/203.15
(Continued)

FOREIGN PATENT DOCUMENTS

CN    203263962    11/2013
EP      1322356     7/2003
EP      2042208     4/2009

OTHER PUBLICATIONS

International Preliminary Report on Patentability re: PCT/US2016/033444 dated Dec. 26, 2017.
(Continued)

*Primary Examiner* — Imani N Hayman
*Assistant Examiner* — Tezita Z Watts
(74) *Attorney, Agent, or Firm* — David R. Crichton; Leo B. Kriksunov

(57) ABSTRACT

The present invention is directed to a device for the expression of a hemostatic powder having an elongated reservoir with a manual air pump, such as a bellows, at a proximal end and an expression port at a distal end. A porous filter is slidably disposed within the reservoir between the bellows and plunger and the expression port, and a spring is disposed within the reservoir between the air pump and the plunger. The powder is disposed within the reservoir between the porous filter and the expression port, and the pump is in a fluid communication with the expression port through the porous filter and through the powder.

17 Claims, 28 Drawing Sheets

(52) U.S. Cl.
CPC ....... *A61L 26/0023* (2013.01); *A61L 26/0066* (2013.01); *A61M 11/006* (2014.02); *A61M 11/007* (2014.02); *A61M 11/008* (2014.02); *A61M 13/00* (2013.01); *A61M 35/003* (2013.01); *A61L 2300/418* (2013.01); *A61L 2300/60* (2013.01); *A61L 2400/04* (2013.01); *A61M 2202/064* (2013.01); *A61M 2205/071* (2013.01); *A61M 2205/073* (2013.01); *A61M 2205/10* (2013.01)

(58) Field of Classification Search
CPC .............. A61M 11/007; A61M 11/008; A61M 2202/064; A61M 13/00; A61M 13/006; A61M 5/281; A61M 5/282; A61M 5/2425; A61M 11/03; A61B 17/3423; A61L 26/0023; A61L 26/0066; A61L 26/009; A61L 2300/60; A61L 2400/04; A61L 2300/418
See application file for complete search history.

(56) References Cited

U.S. PATENT DOCUMENTS

| | | | |
|---|---|---|---|
| 7,540,282 B2 | 6/2009 | O'Leary | |
| 7,923,031 B2 | 4/2011 | Moller | |
| 8,056,762 B2 | 11/2011 | Wright et al. | |
| 9,682,391 B2* | 6/2017 | Baillet | A61M 11/02 |
| 2003/0111131 A1 | 6/2003 | Zhu et al. | |
| 2005/0098172 A1* | 5/2005 | Anderson | A61M 15/08 128/200.23 |
| 2007/0235029 A1 | 10/2007 | Zhu et al. | |
| 2008/0210229 A1* | 9/2008 | Corbacho | A61M 15/0028 128/200.22 |
| 2009/0166379 A1* | 7/2009 | Wright | A61M 15/0028 222/80 |
| 2009/0236374 A1* | 9/2009 | Pardes | A61F 9/0008 222/494 |
| 2011/0178495 A1* | 7/2011 | Ji | A61M 13/00 604/500 |
| 2012/0103332 A1* | 5/2012 | Parsons | A61M 15/0028 128/203.15 |
| 2016/0249966 A1* | 9/2016 | McKay | G06F 16/972 210/767 |
| 2016/0250417 A1* | 9/2016 | Olson | A61M 5/2033 604/228 |
| 2017/0304562 A1* | 10/2017 | Riebman | A61B 17/00491 |

OTHER PUBLICATIONS

International Search Report PCT/US2016/0334444 dated Aug. 8, 2016.

* cited by examiner

Inventive device horizontal

HEMOSTATIC POWDER DELIVERY DEVICES AND METHODS

FIELD OF THE INVENTION

The present invention is directed to Hemostatic Powder Delivery Devices and Methods, particularly to hand-operated devices which can be operated with one hand to express topical absorbable hemostatic powders directly onto a wound.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and fibrinogen.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. A number of methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber. Examples of such hemostatic wound dressings commercially available include SURGICEL SNoW® Absorbable Hemostat; SURGICEL® Original Absorbable Hemostat; SURGICEL® FIBRILLAR™ Absorbable Hemostat; SURGICEL NU-KNIT® Absorbable Hemostat; all available from Johnson & Johnson Wound Management Worldwide, a division of Ethicon, Inc., Somerville, N.J., a Johnson & Johnson Company. Other examples of commercial resorbable hemostats containing oxidized cellulose include GelitaCel™ resorbable cellulose surgical dressing from Gelita Medical BV, Amsterdam, The Netherlands. The commercially available oxidized cellulose hemostats noted above are knitted or nonwoven fabrics having a porous structure for providing hemostasis.

Hemostatic materials can also be provided in powdered form, such as for example powders based on purified plant starch, clay, zeolite granules, fibrinogen, thrombin, mixtures of fibrinogen and thrombin, etc. There is a need in delivering these and similar hemostatic materials in a powder form to the surface of tissue or wound for controlling bleeding.

The existing devices for delivering hemostatic powders lack uniformity in delivery, with quantity of powder delivered at the beginning of expression varying from quantity of powder delivered at the end of the expression. Also the existing device have significant variability in powder delivery under varying angles of spray, i.e. when orientation is changing from horizontal to vertical and any angle in-between. Further, the existing devices might not perform well in laparoscopic delivery modes, may clog, or may express some powder prior to actuation, i.e. due to powder leakage from the devices.

U.S. Pat. No. 6,866,039 discloses a dispensing apparatus for dispensing a powdered product comprising: a housing defining an outlet, a shaft having a storage chamber therein for a powdered product provided with a first inlet and a first outlet, a sheathing member slidably mounted on the shaft and having a second inlet and a second outlet closed by a frangible membrane, and a variable volume member operatively connected to the shaft; wherein the shaft is moveable, on operation of the variable volume member to reduce the variable volume so as to pressurize gas in an interior of the variable volume member, from an initial storage position in which the first and second inlets are out of alignment so as to close a gas flow path, to a dispensing position, in which the first and second inlets are brought into alignment by action of the housing against the sheathing member and in which the frangible membrane is ruptured by the shaft so as to open the gas flow path, such that pressurized gas from the interior of the variable volume member is discharged along the gas flow path comprising the first and second inlets, storage chamber, second outlet and first outlet, to thereby entrain powdered product and dispense it through the housing outlet.

U.S. Pat. No. 8,056,762 discloses a hand-held dispenser for dispensing a pharmaceutical product, the dispenser comprising: a housing providing a duct; a frangible membrane provided in the duct; a probe with a piercing tip mounted in the duct, the probe being arranged such that, in use, the piercing tip pierces the frangible membrane; an air compression device to compress air for expelling a pharmaceutical product through the probe; and a channel to substantially equalize the pressure in the air compression device and the pressure above the frangible membrane, wherein the frangible membrane is provided on a sheath which comprises a first larger diameter portion and a second axially spaced smaller diameter portion defining an external shoulder therebetween, and the inside surface of the duct has a corresponding internal shoulder to be engaged by the external shoulder of the sheath and an axial spacer is provided on one or both of the external and internal shoulders to maintain the channel past the engaged shoulders.

Published U.S. Patent Application 2012/0103332 discloses a powder delivery device, comprising: a body; a nasal adapter; a piercing device between the nasal adapter and the body; a blister between the piercing device and the body, wherein the blister contains a powder; a bellows; a spring; and an actuator.

U.S. Pat. No. 7,923,031 discloses a powder delivery system comprising: a chamber storing a hemostatic composition comprising dry gelatin powder having a mean particle size in the range of 30-250 micrometers and hyaluronic acid, said chamber having at least one discharge opening sized for distributing said composition.

European Publication No. 1,322,356 discloses a device for delivering multiple doses of physiologically active agent in powdered form, the device comprising: a manually rechargeable air reservoir; a powder container defining therein a plurality of individual receptacles, each receptacle containing a discrete metered dose of powder, a powder delivery passage for the forced flow therethrough to a patient of air with a said metered dose of powder entrained therein so as substantially to empty a said receptacle, a closure for restricting the unwanted ingress of moisture into the device via said passage when the device is not in use; and a container indexing mechanism for indexing movement of said container to move a substantially empty said receptacle out of communication with said powder delivery passage and to move a fresh powder-containing said receptacle into communication with said powder delivery passage; wherein the device is constructed and arranged so that the action of opening or closing said closure (i) operates said container indexing mechanism and (ii) charges the air reservoir with air.

European Publication No. 2,042,208 discloses a dispensing device for dispensing a formulation as a spray, wherein the dispensing device is adapted to receive or comprises a storage device with at least one or multiple, preferably separate and pre-metered doses of the formulation, wherein the dispensing device comprises a means for pressurizing gas, in particular air, or an air inlet for generating or allowing a gas stream flowing through the storage device for dispensing a dose of the formulation, characterized in that the dispensing device is designed such that pressure pulses are generated in the gas stream during dispensing one dose and/or the direction of gas flow alternates during dispensing one dose.

U.S. Pat. No. 7,540,282 discloses an inhaler, comprising: a sealed reservoir including a dispensing port; a linear channel communicating with the dispensing port and including a pressure relief port; a conduit providing fluid communication between an interior of the sealed reservoir and the pressure relief port of the channel; a cup assembly movably received in the channel and including, a recess adapted to receive medicament from the reservoir when aligned with the dispensing port, a first sealing surface adapted to seal the dispensing port when the recess is not aligned with the dispensing port, and a second sealing surface adapted to seal the pressure relief port when the recess is aligned with the dispensing port and to unseal the pressure relief port when the recess is not aligned with the dispensing port.

Chinese Patent publication No. 203263962 discloses a utility model that relates to a hemostatic dry powder spraying bottle. The hemostatic dry powder spraying bottle comprises a bottle body made of medical plastic, an inner spraying pipe made of medical plastic, an outer sleeve cap and a handle made of medical plastic, wherein a groove which allows the bottle body to stretch in the axial direction of the bottle body is formed in the outer surface of the bottle body, the inner spraying pipe is arranged on the top of the bottle body in a screwed mode through threads, the inner spraying pipe is sleeved with the outer sleeve cap, the lower end of the outer sleeve cap is connected with the bottle body, and the handle is fixedly connected with the bottle body. The hemostatic dry powder spraying bottle is simple and novel in structure, low in cost, convenient to use, even in exerted force, complete in powder spraying and good in powder spraying effect and hemostatic effect.

There is a need in improved delivery devices for delivering hemostatic powders to the surface of tissue or wound for controlling bleeding.

SUMMARY OF THE INVENTION

The present invention relates to a device for expression of a powder, comprising: an elongated hollow reservoir, the reservoir having a manual air pump attached to the reservoir, the reservoir having an expression port at a distal end of said reservoir, a porous filter slidably disposed within the reservoir between said air pump and said expression port; a spring disposed within the reservoir between the air pump and the filter; wherein the powder is disposed within the reservoir between the filter and the expression port, and wherein the pump is in a fluid communication with the expression port through the porous filter and through the powder.

FIG. 21 shows an alternative embodiment of the powder delivery device of the present invention.

FIG. 22 shows an alternative embodiment of the powder delivery device of the present invention.

FIG. 23 shows a schematic rendering of an alternative embodiment of the powder delivery device of the present invention.

FIG. 24 shows a schematic rendering of a comparative device used in testing.

FIG. 25 shows a chart of the quantities of powder expressed from the comparative device with each expression or powder burst plotted as cumulative grams expressed relative to the sequential number of expression, using vertical orientation of the comparative device.

Figure 26:
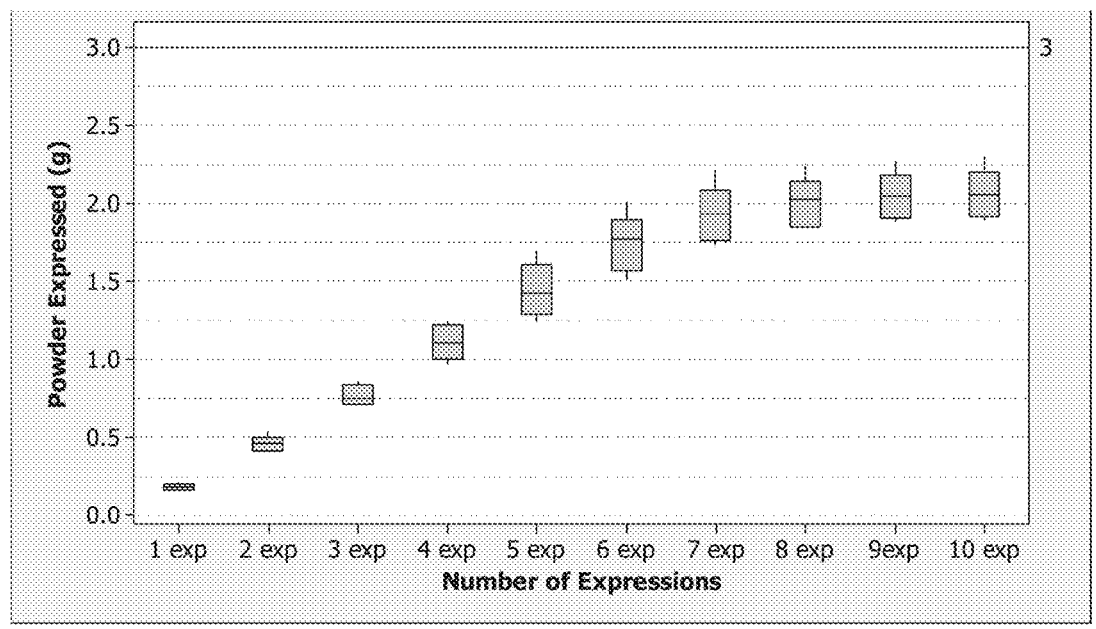

FIG. 26 shows a chart of the quantities of powder expressed from the comparative device with each expression or powder burst plotted as cumulative grams expressed relative to the sequential number of expression, using horizontal orientation of the comparative device.

Figure 27:
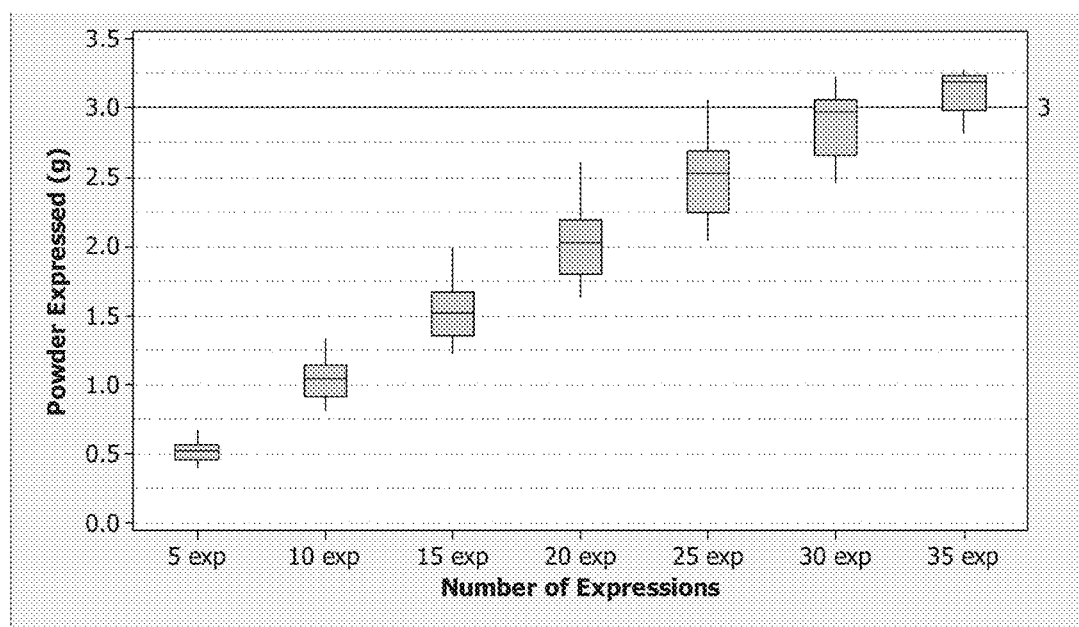

FIG. 27 shows a chart of the quantities of powder expressed from the device of the present invention plotted as cumulative grams expressed relative to the sequential number of expressions, using vertical orientation of the inventive device.

Figure 28:
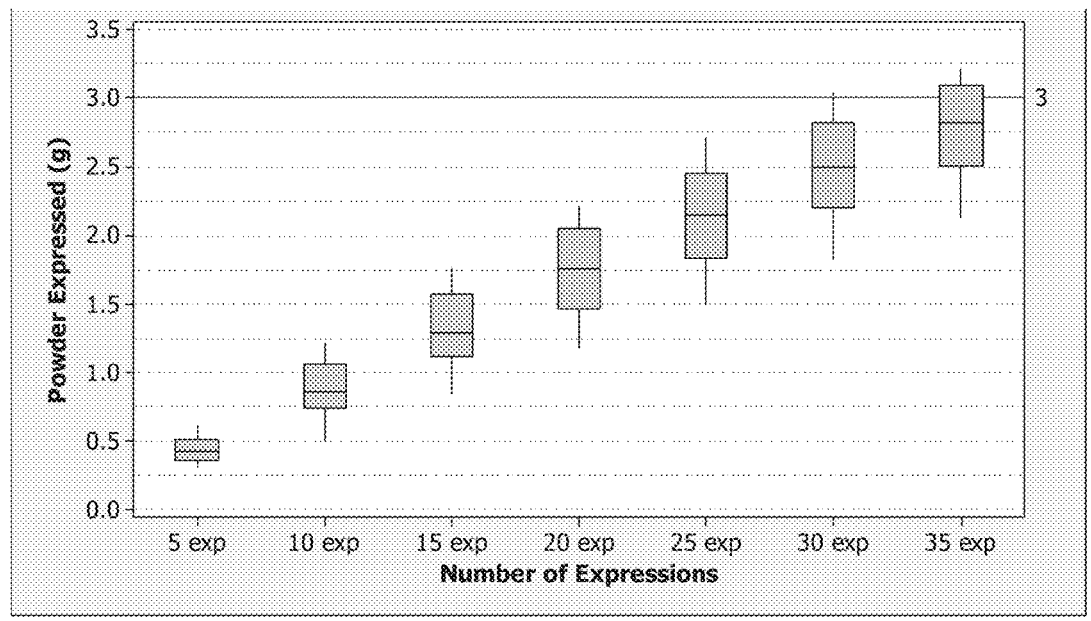

FIG. 28 shows a chart of the quantities of powder expressed from the device of the present invention plotted as cumulative grams expressed relative to the sequential number of expressions, using horizontal orientation of the inventive device.

DETAILED DESCRIPTION

Figure 5:
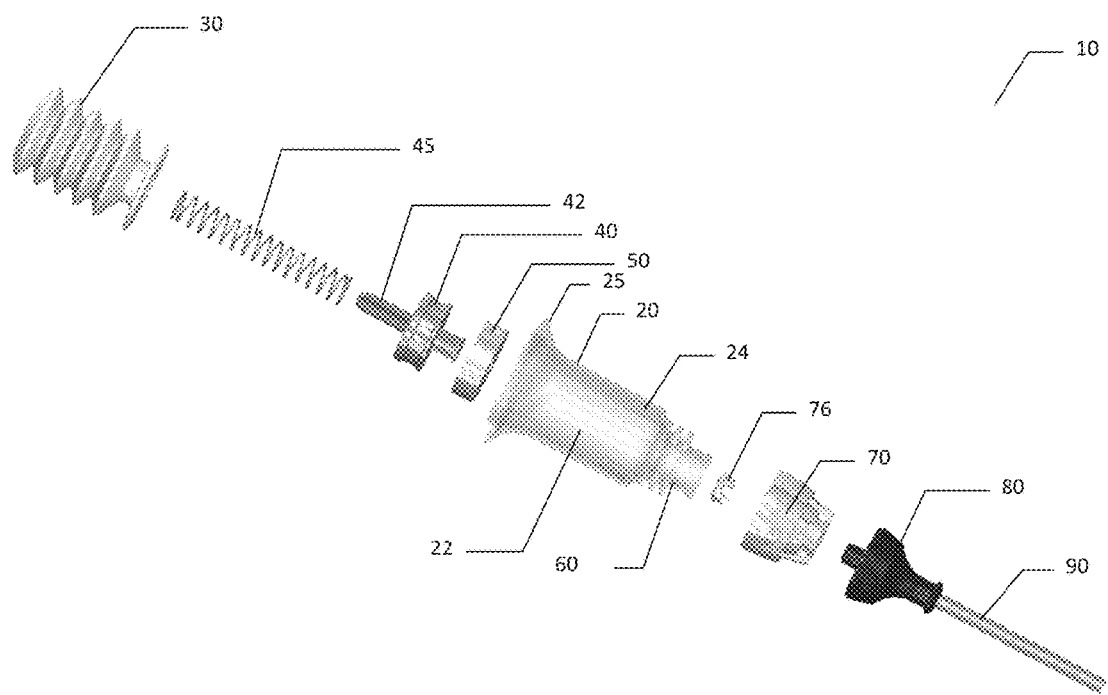
FIG. 5 shows an embodiment of the powder delivery device of the present invention in an exploded view.
Figure 6:
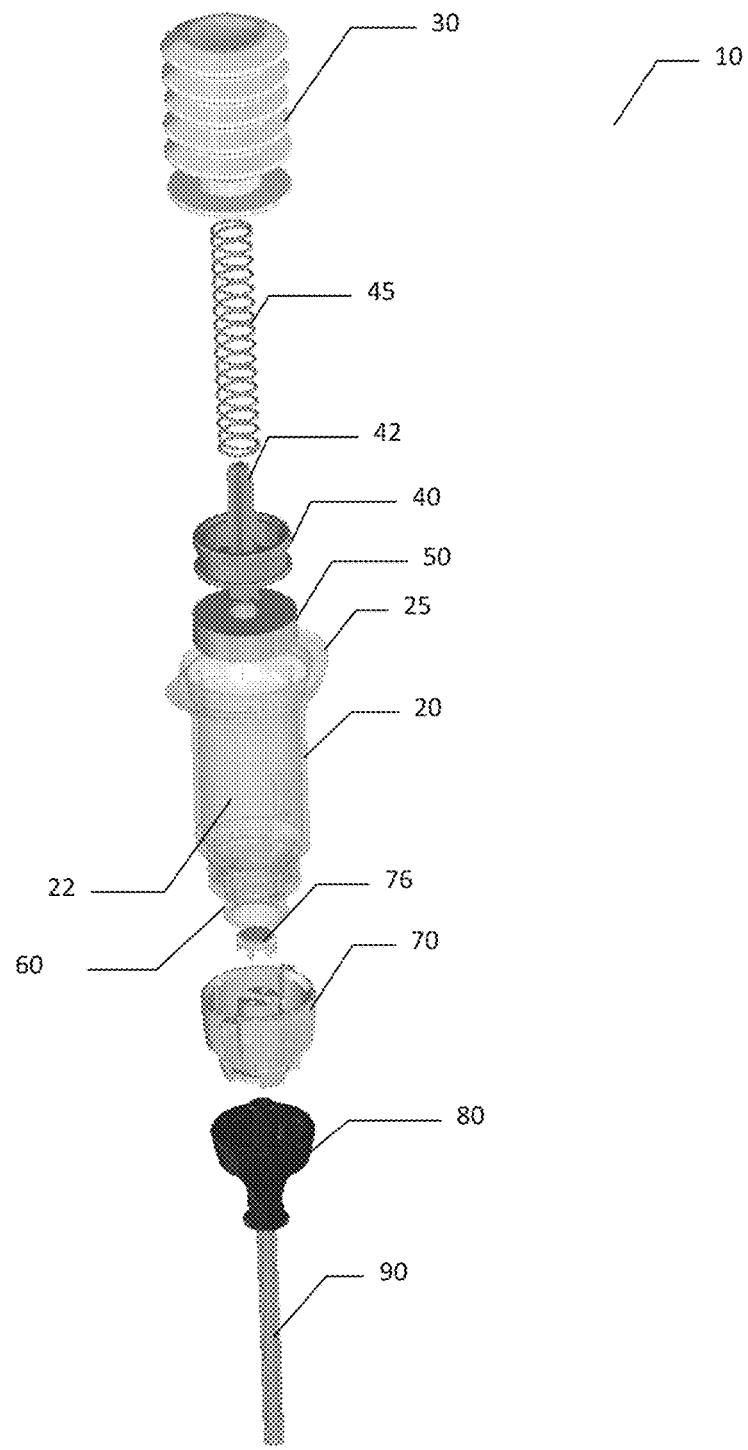
FIG. 6 shows an embodiment of the powder delivery device of the present invention in an exploded view.
Figure 7:
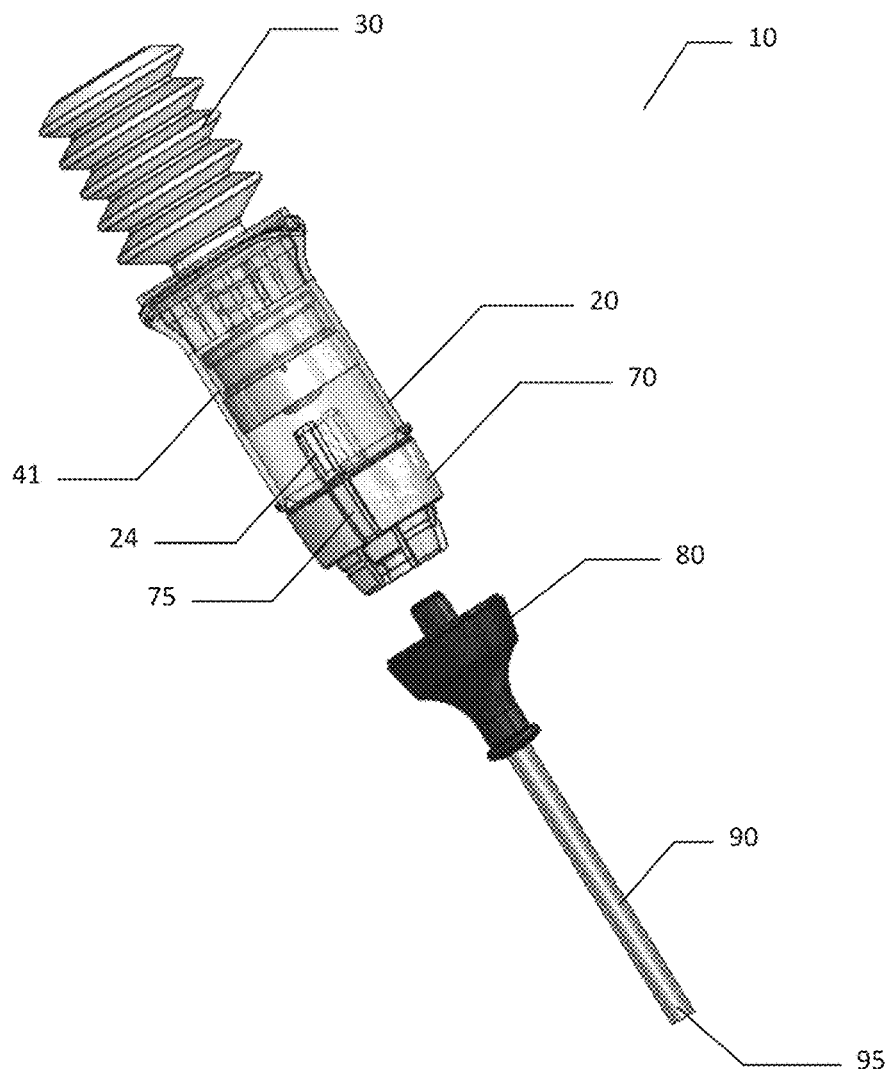
FIG. 7 shows an embodiment of the powder delivery device of the present invention in a partially disassembled view.
Figure 8:
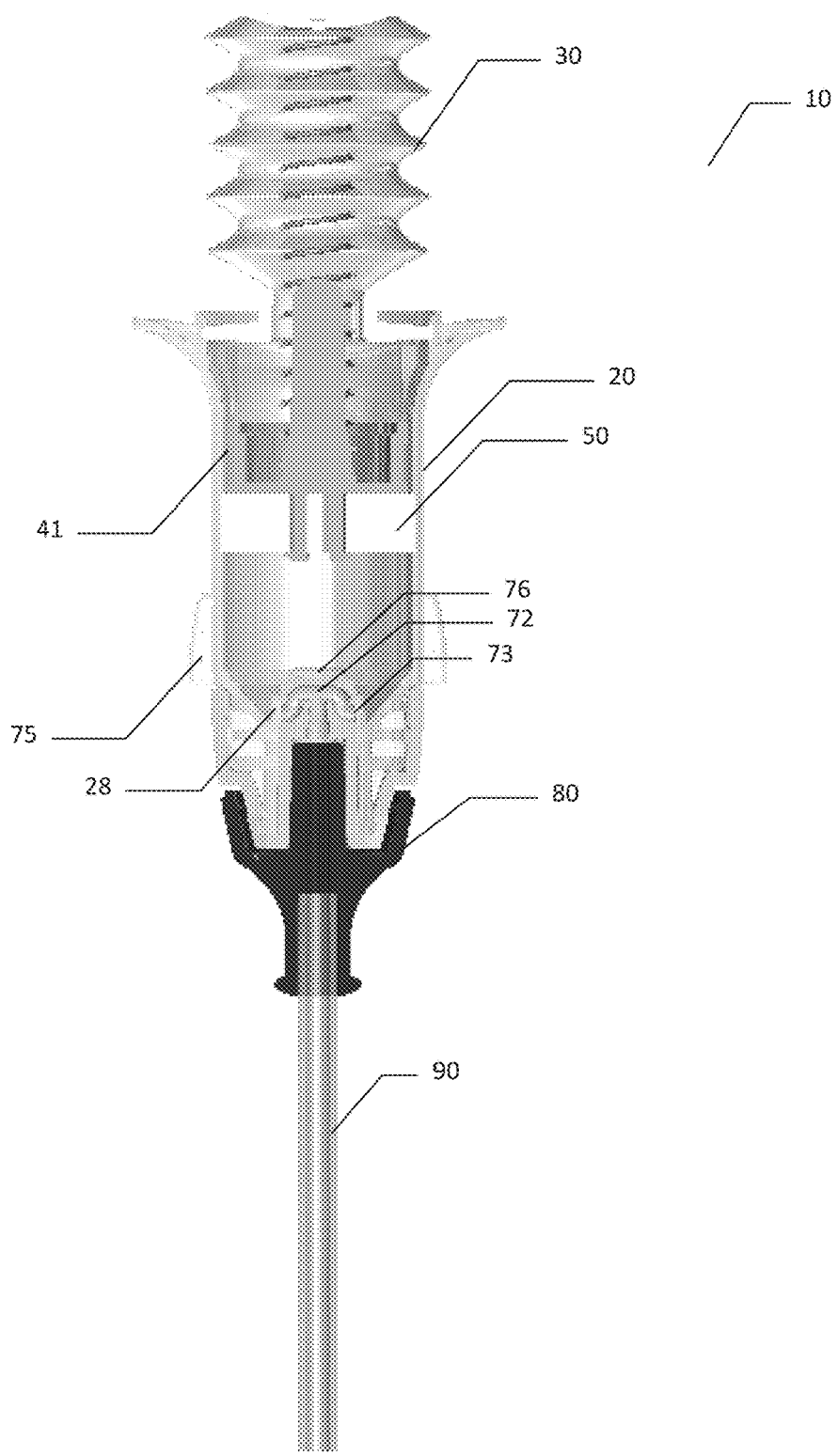
FIG. 8 shows an embodiment of the powder delivery device of the present invention in a cross-sectional view.
Figure 11:
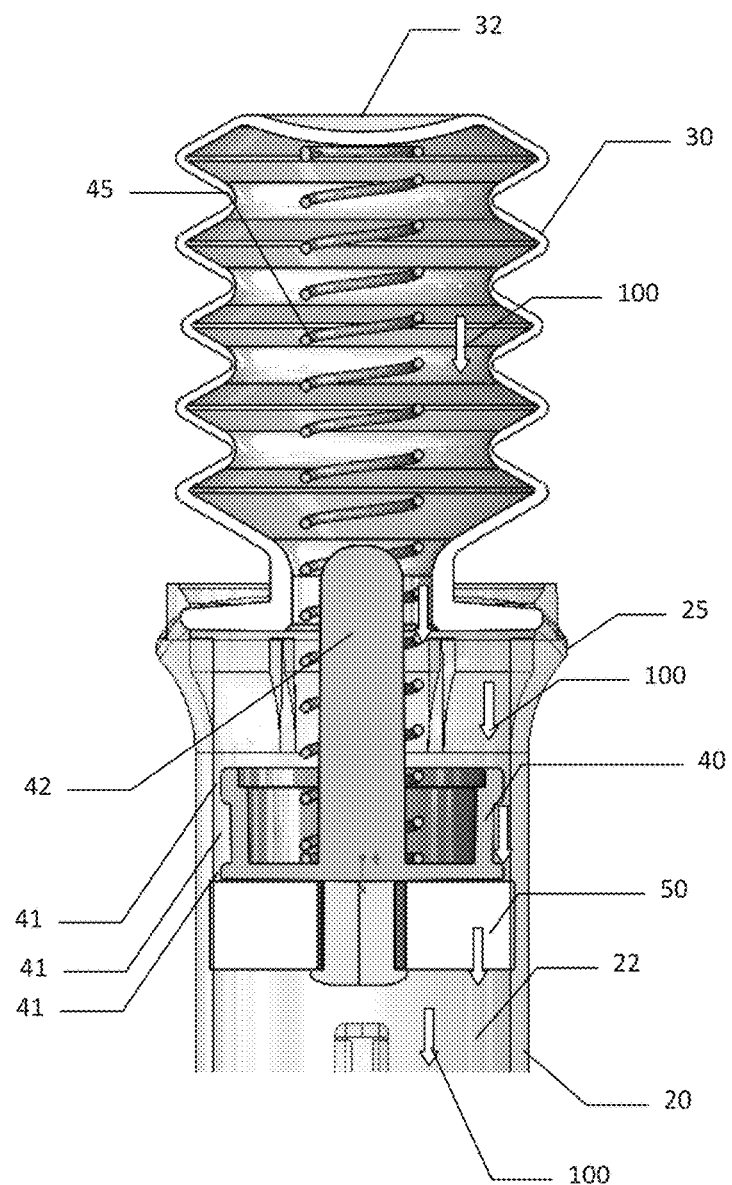
FIG. 11 shows an embodiment of the powder delivery device of the present invention in a cross-sectional view.
Figure 12:
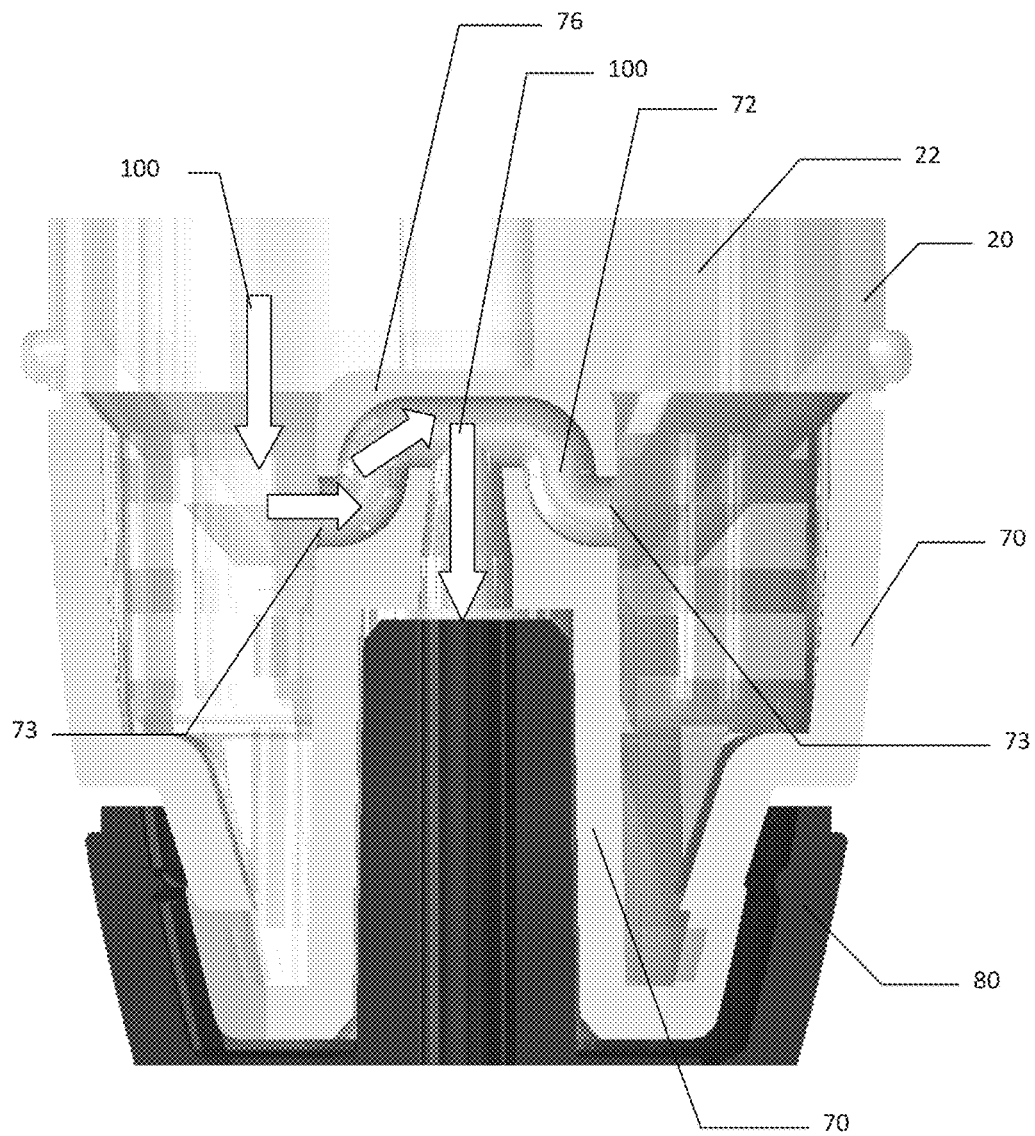
FIG. 12 shows an embodiment of the powder delivery device of the present invention in a cross-sectional view.
Figure 13:
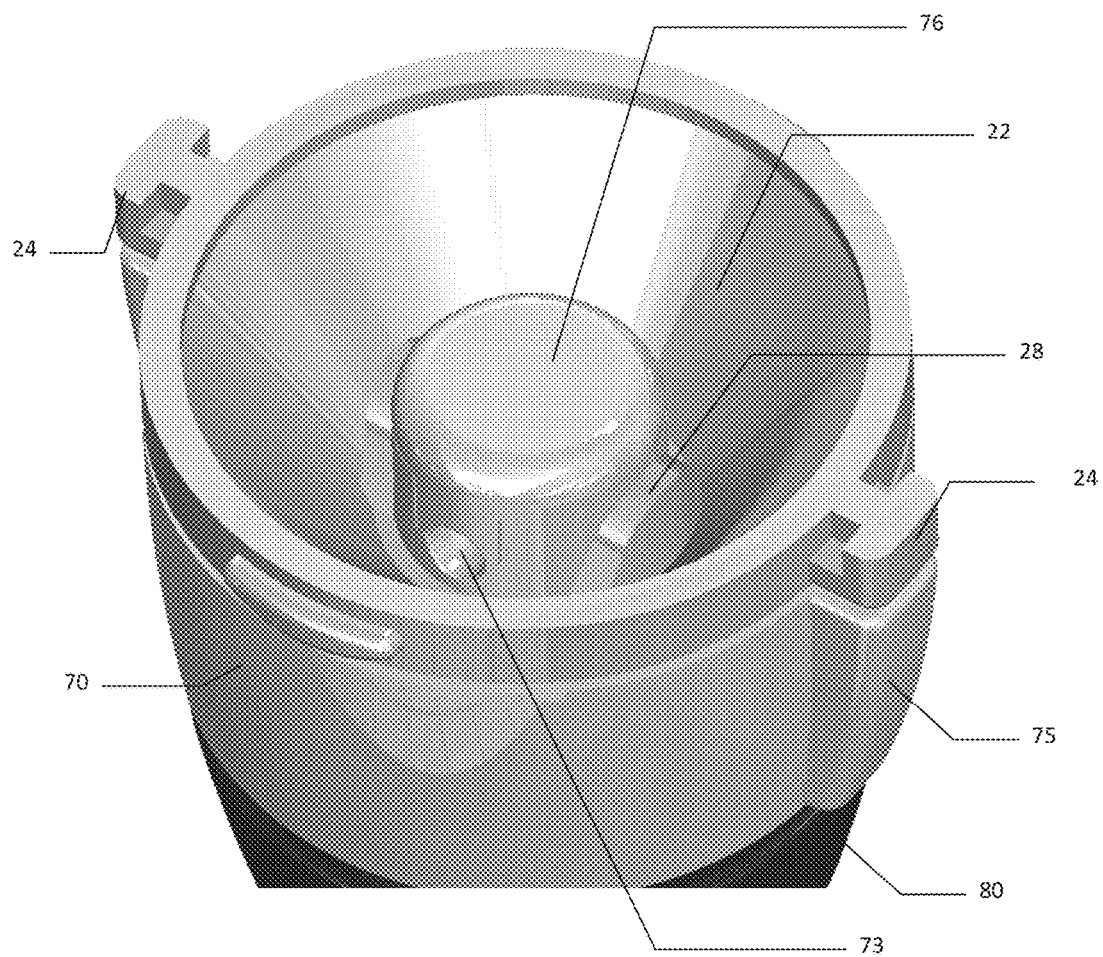
FIG. 13 shows an embodiment of the powder delivery device of the present invention.
Figure 14:
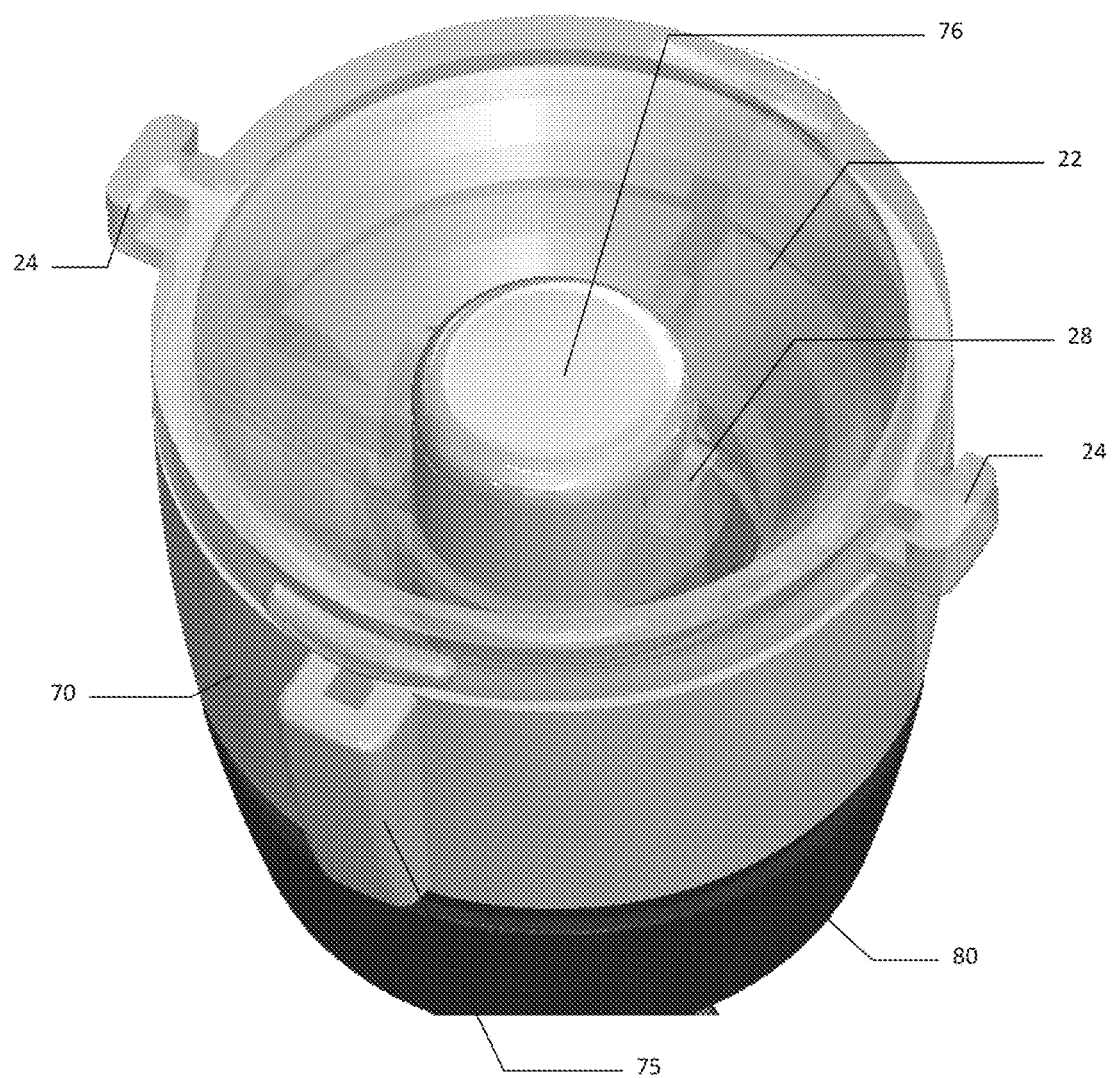
FIG. 14 shows an embodiment of the powder delivery device of the present invention.

Embodiments of the powder delivery device 10 of the present invention are shown in FIGS. 1-4 in prospective view, FIGS. 5-7 in an exploded view, FIGS. 8-12 in a cross-sectional view, FIGS. 13-14 in a partial prospective internal view. Device 10 comprises a hollow tubular body or reservoir 20 on which a manual air pump, such as a compressible elastic bulb (not shown) or bellows 30 (as shown) is mounted at a proximate end 11. Reservoir 20 has an optional hand grip 25 at proximate end 11. Within reservoir 20 is positioned a plunger 40 with an optional filter 50 mounted on plunger 40. Plunger 40 with filter 50 is mounted slidably within reservoir 20 and is capable of advancing within reservoir 20 towards distal end 12. At distal end 12 of reservoir 20 is positioned an open-ended port 60 which is in fluid communication with reservoir 20. Onto port 60 is axially mounted an optional powder trap 70 onto which is axially mounted a hub 80, which is integrated with a tubular expression cannula 90 having a cannula exit 95. Optional O-rings can be provided (not shown) for air-tight mounting of powder trap 70 and hub 80.

Plunger 40 has an optional plunger stem 42 axially extending from plunger 40 rearward towards proximal end 11. On plunger stem 42 is positioned spring 45. Spring 45 is positioned between bellows 30 and plunger 40 and partially inside bellows 30, more specifically between top of bellows 32 and plunger 40. Plunger 40 and filter 50 are coaxially and slidably moveable within reservoir 20. Plunger 40 forms an optional gap 41 between reservoir 20 and plunger 40, with gap 41 ranging from about 0.01 mm to about 2 mm, such as 0.1 mm, 0.2 mm, 0.3 mm or 0.5 mm. Alternatively to optional gap 41, or in addition to a narrow gap 41, at least one aperture in plunger 40 (aperture not shown) provides for a path for gas to pass from proximal side of plunger 40 to distal side of plunger 40.

Microporous filter 50 snugly and slidably fits within reservoir 20 and moves together with plunger 40 onto which filter 50 is mounted. A portion of reservoir 20 between filter 50 and port 60 is a powder compartment 22, filled with hemostatic powder (not shown). Volume of powder compartment 22 is changing depending on the position of plunger 40 and filter 50, and as plunger 40 advances towards distal end 12 or towards port 60, volume of powder compartment 22 decreases.

As shown in FIGS. 5, 6, 8-10, 12-14, optional powder trap 70 is mounted onto port 60 by any known means, such as by snap-on mounting. Optional powder trap 70 provides for a tortuous path for the powder and gas exiting powder compartment 22. Powder trap is formed by trap lid 76 covering tortuous path 72 which is a channel having several bends and starting with an orifice 73 located within powder compartment 22. As further shown in FIGS. 9, 12 tortuous path 72 results in turning of the direction along which air and powder are advancing within device 10, particularly turning from going generally from proximal towards distal direction, i.e. from powder compartment 22 to cannula exit 95, to going a short distance in other direction, such as in sideways direction and/or in opposite direction, i.e. perpendicular to main axis of device 10 or rearwards, from distal end 12 towards proximal end 11. This change in the direction along which air and powder advancing within device 10 along tortuous path 72 is shown schematically by arrows 100 which indicate air and powder advancement from proximal end 11 towards distal end 12, with a brief intermittent change in the direction when advancing through tortuous path 72.

Powder trap 70 prevents hemostatic powder (not shown) in powder compartment 22 from exiting device 10 via cannula 90 when no air flow is present, i.e. prevents loss of powder especially when device 10 is positioned with cannula exit 95 points generally downwards, especially when device 10 is subject to shaking or vibration or any variable acceleration movements. Powder trap 70 prevents unintentional expression of small quantities of powder from powder compartment 22, while allowing powder expression when driven by air flow.

Optional reservoir ridges 24 and powder trap ridges 75 are grasping features located on the outside surface of reservoir 20 and powder trap 70 and enable an optional blocking feature of device 10, providing for blocking orifices 73 serving as entrance to tortuous path 72. Using powder trap ridges 75 powder trap can be rotated about reservoir 20 to which powder trap 70 is snapfit and rotatably attached at port 60. In the embodiments of FIGS. 2, 4, 7, 9, 10, 12, 13, when reservoir ridges 24 and powder trap ridges 75 are aligned, orifice 73 is open into powder compartment 22 and not blocked by blocking member 28 within reservoir 20 (FIG. 13) so that powder and air can enter tortuous path 72 and exit device 10 via cannula exit 95.

In the embodiments of FIGS. 1, 3, 8, 14, when reservoir ridges 24 and powder trap ridges 75 are not aligned or are rotated at 90° to each other, orifice 73 is blocked by blocking member 28 within reservoir 20 (FIG. 14) and thus orifice 73 is closed preventing powder and air entering tortuous path 72 from powder compartment 22 and exiting device 10 via cannula exit 95. This optional blocking feature prevents inadvertent activation of device 10 and inadvertent expression of powder.

Figure 9:
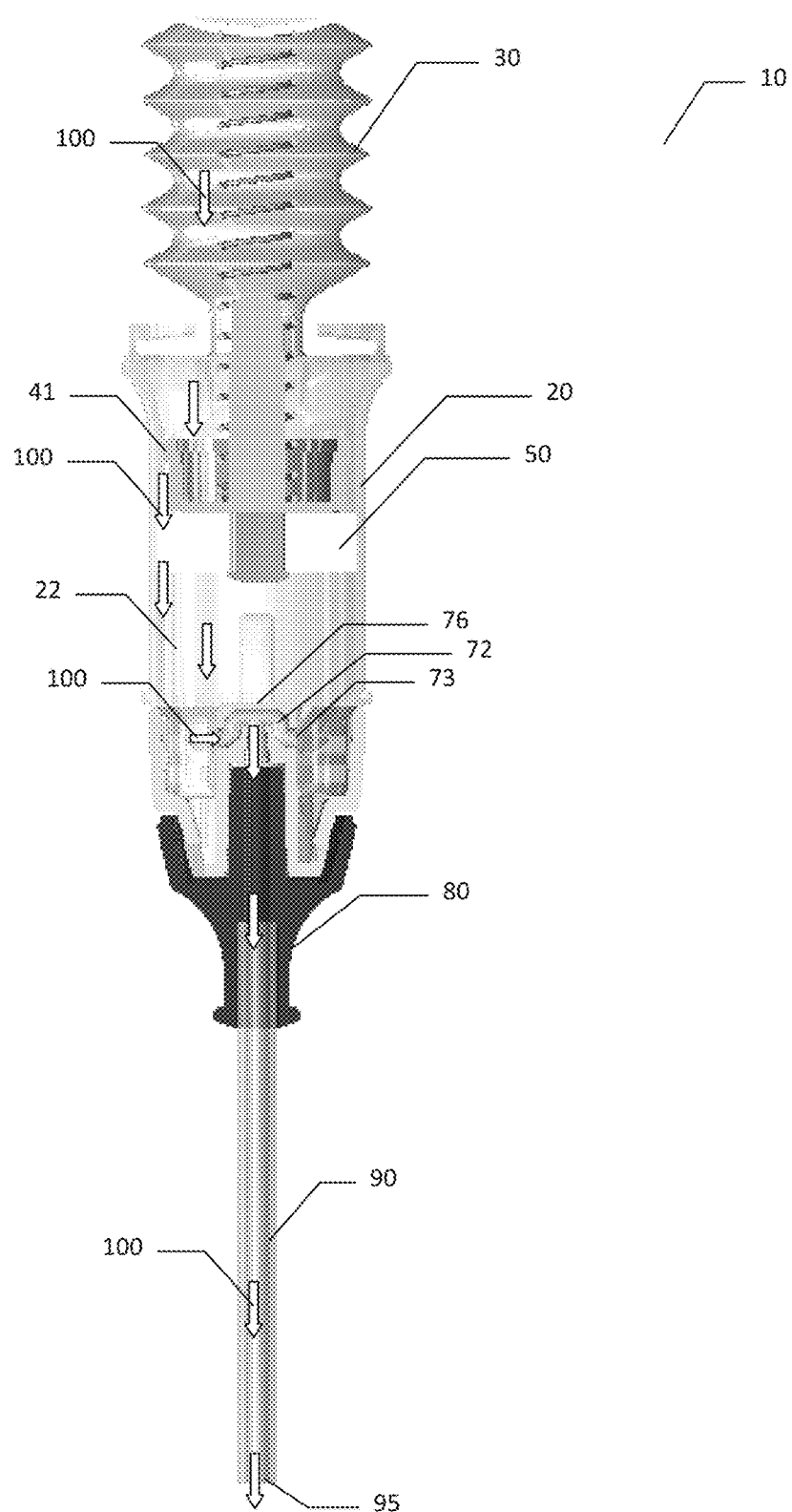
FIG. 9 shows an embodiment of the powder delivery device of the present invention in a cross-sectional view.
Figure 10:
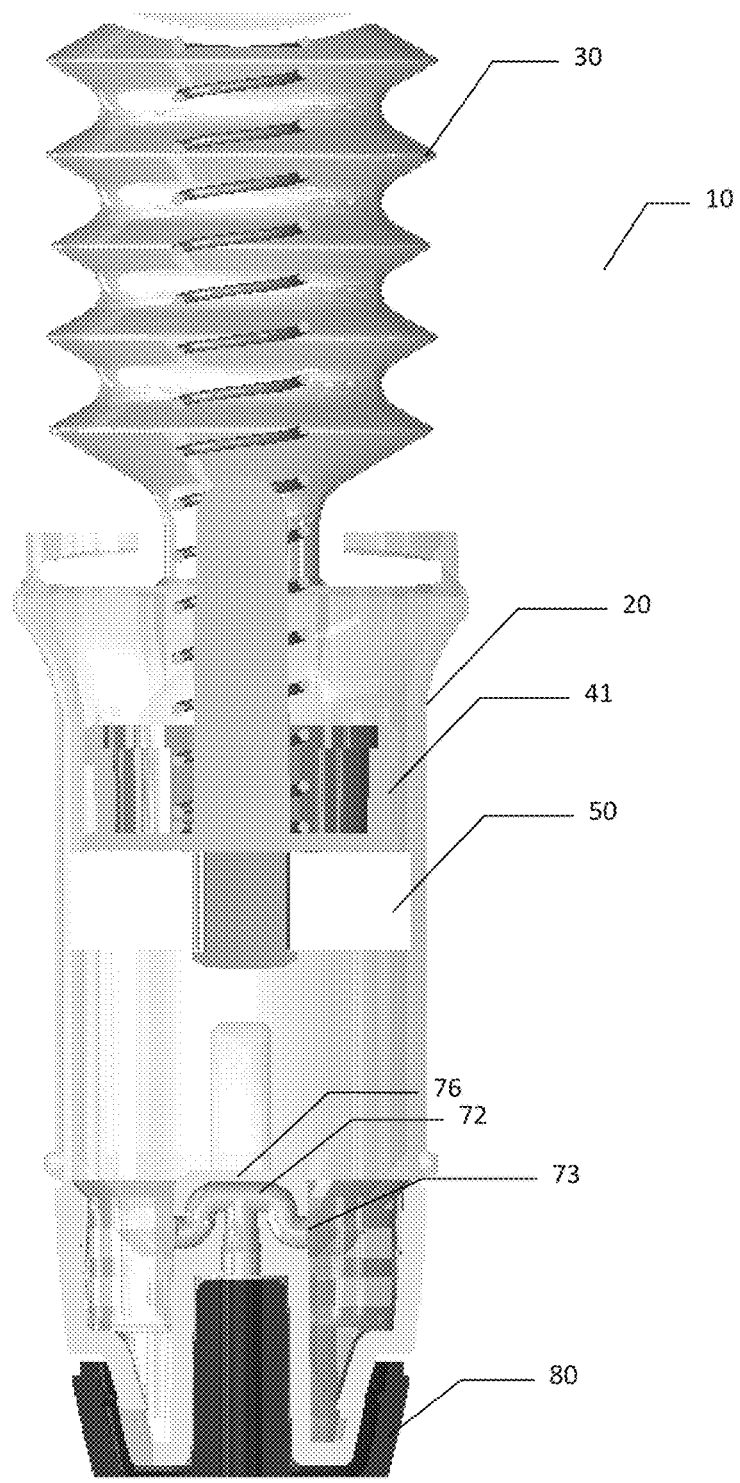
FIG. 10 shows an embodiment of the powder delivery device of the present invention in a cross-sectional view.

Referring to FIGS. 9, 11, 12, the flow of air and/or air with entrained powder from powder compartment 22 is schematically indicated by arrows 100. Bellows 30 is in fluid communication with cannula exit 95 through gap 41, filter 50, powder compartment 22, tortuous path 72, hub 80, and cannula 90. Upon compression of bellows 30 air moves from bellows 30 via gap 41 and through filter 50 into powder compartment 22. From powder compartment 22, as also is schematically indicated by arrows 100, powder and air stream are entering tortuous path 72 through orifice 73 and then move from tortuous path 72 into hub 80, cannula 90, exiting device 10 via cannula exit 95.

Figure 15:
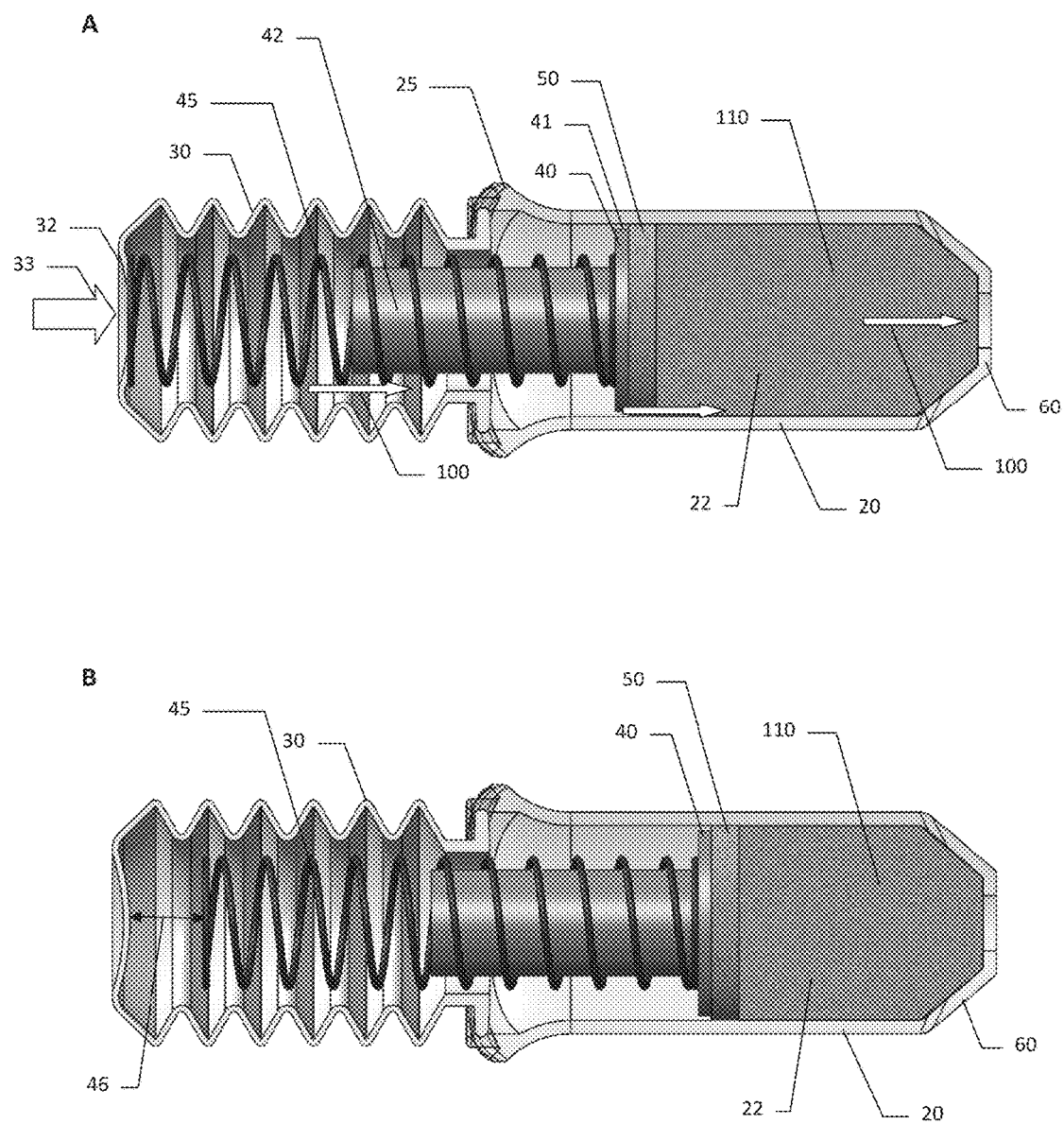
FIG. 15 shows an embodiment of the powder delivery device of the present invention in a cross-sectional view.
Figure 16:
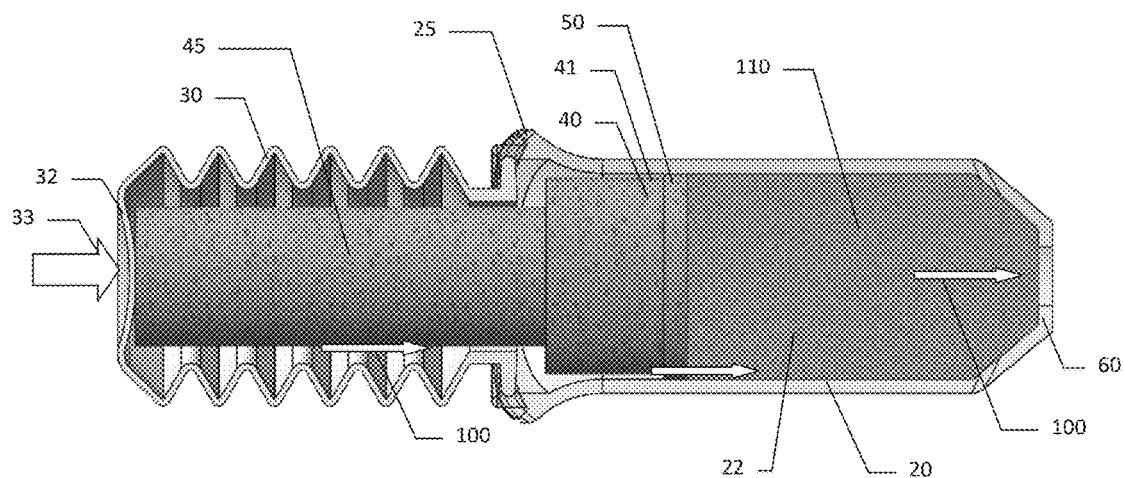
FIG. 16 shows an alternative embodiment of the powder delivery device of the present invention in a cross-sectional view.
Figure 16:
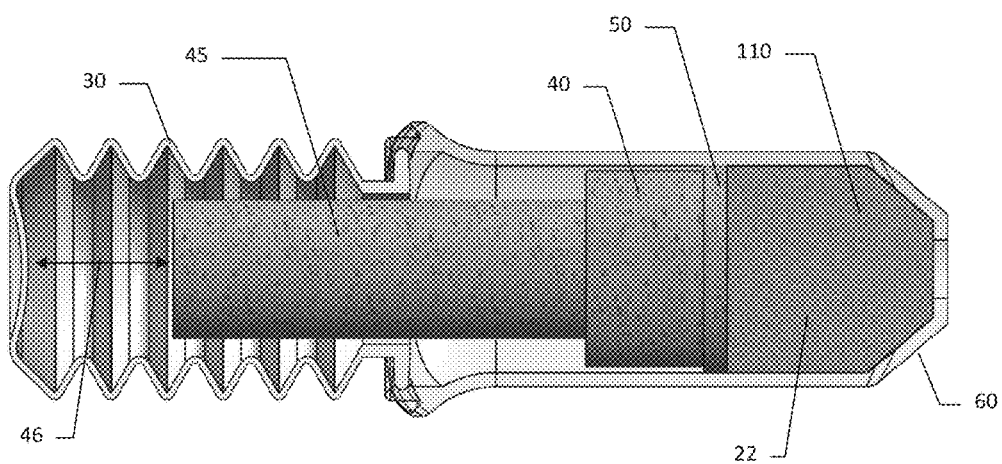
Figure 17:
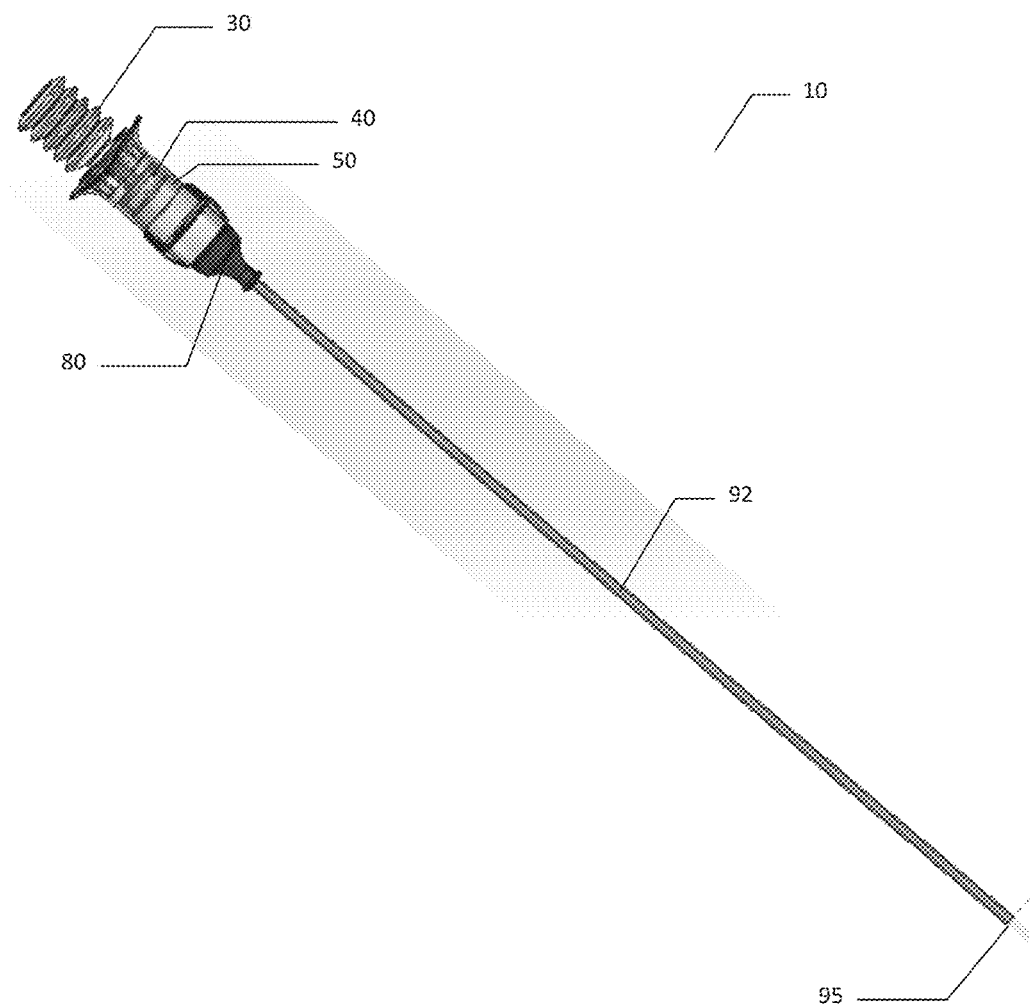
FIG. 17 shows an embodiment of the powder delivery device of the present invention with elongated cannula attached.
Figure 18:
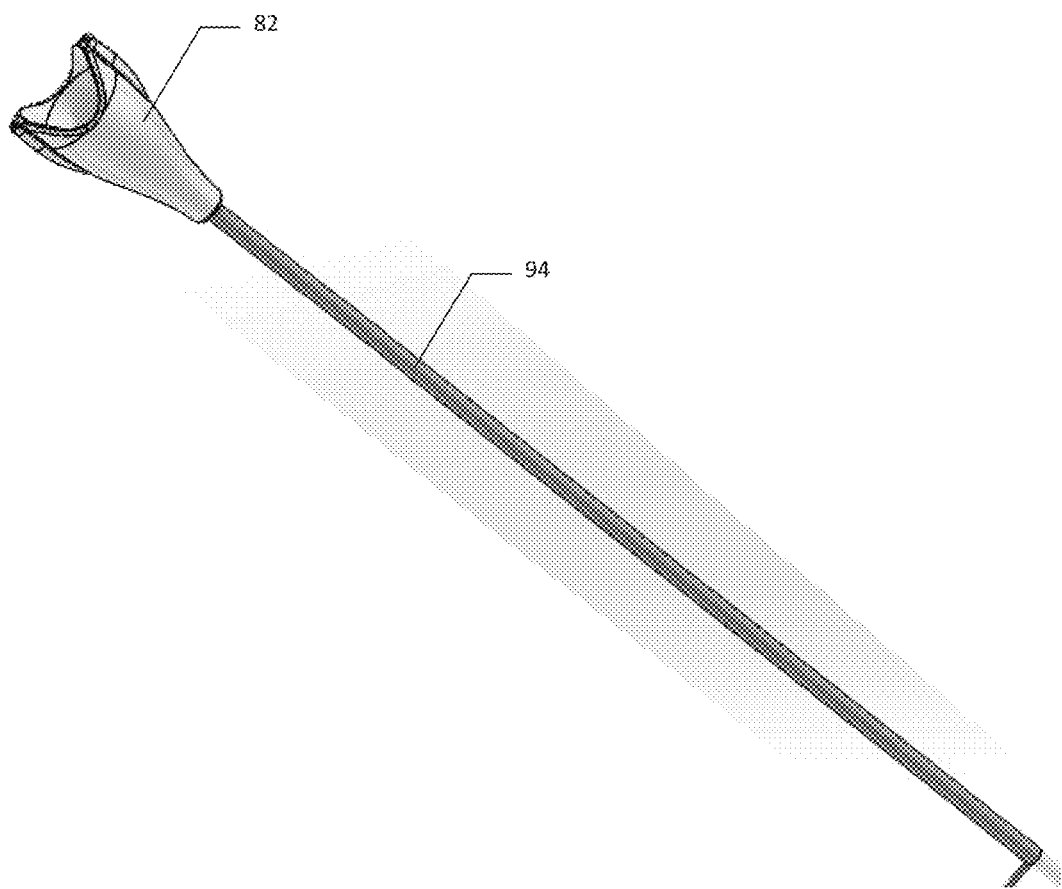
FIG. 18 shows rigid shaft with a shroud.
Figure 19:
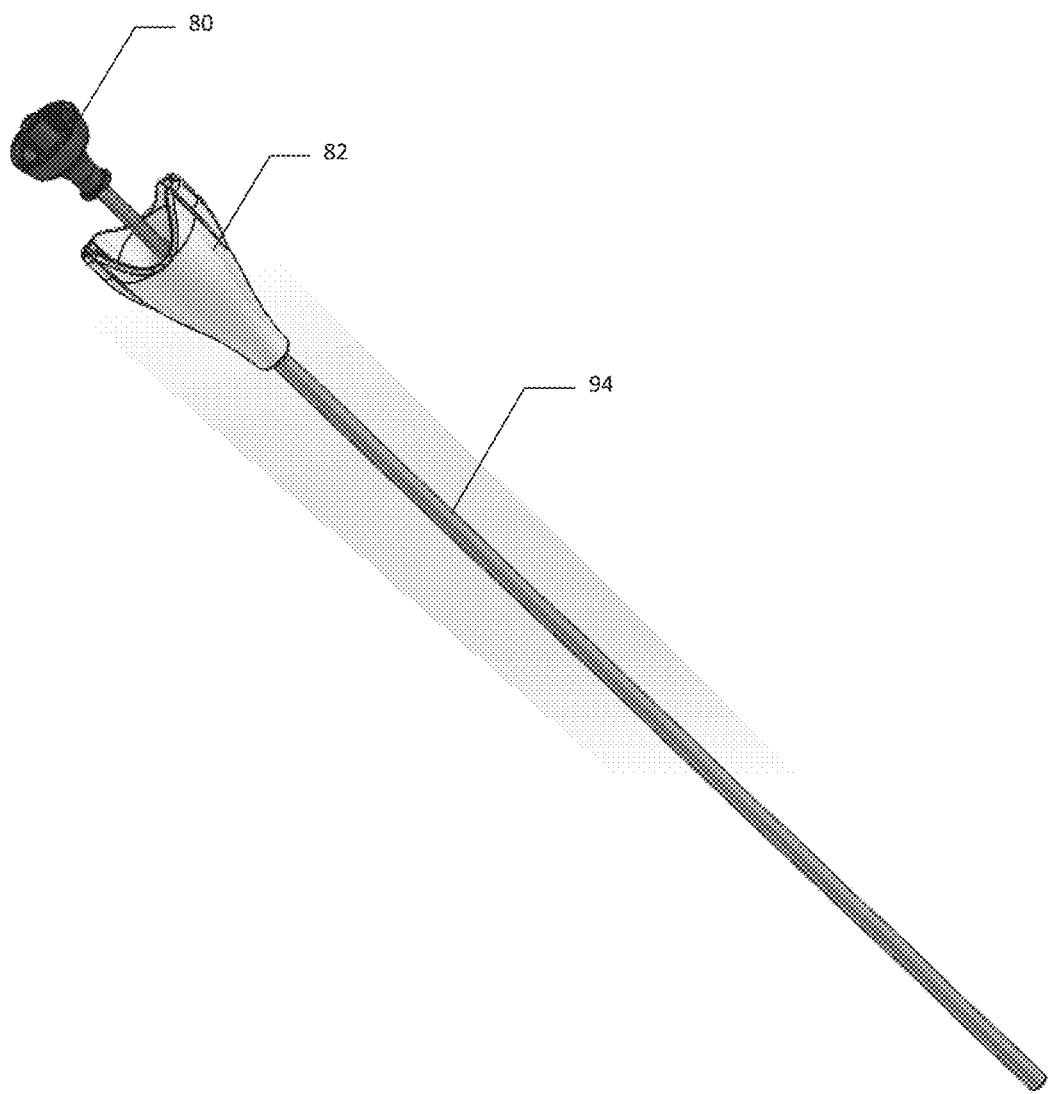
FIG. 19 shows elongated cannula partially inserted into the rigid shaft with a shroud.
Figure 20:
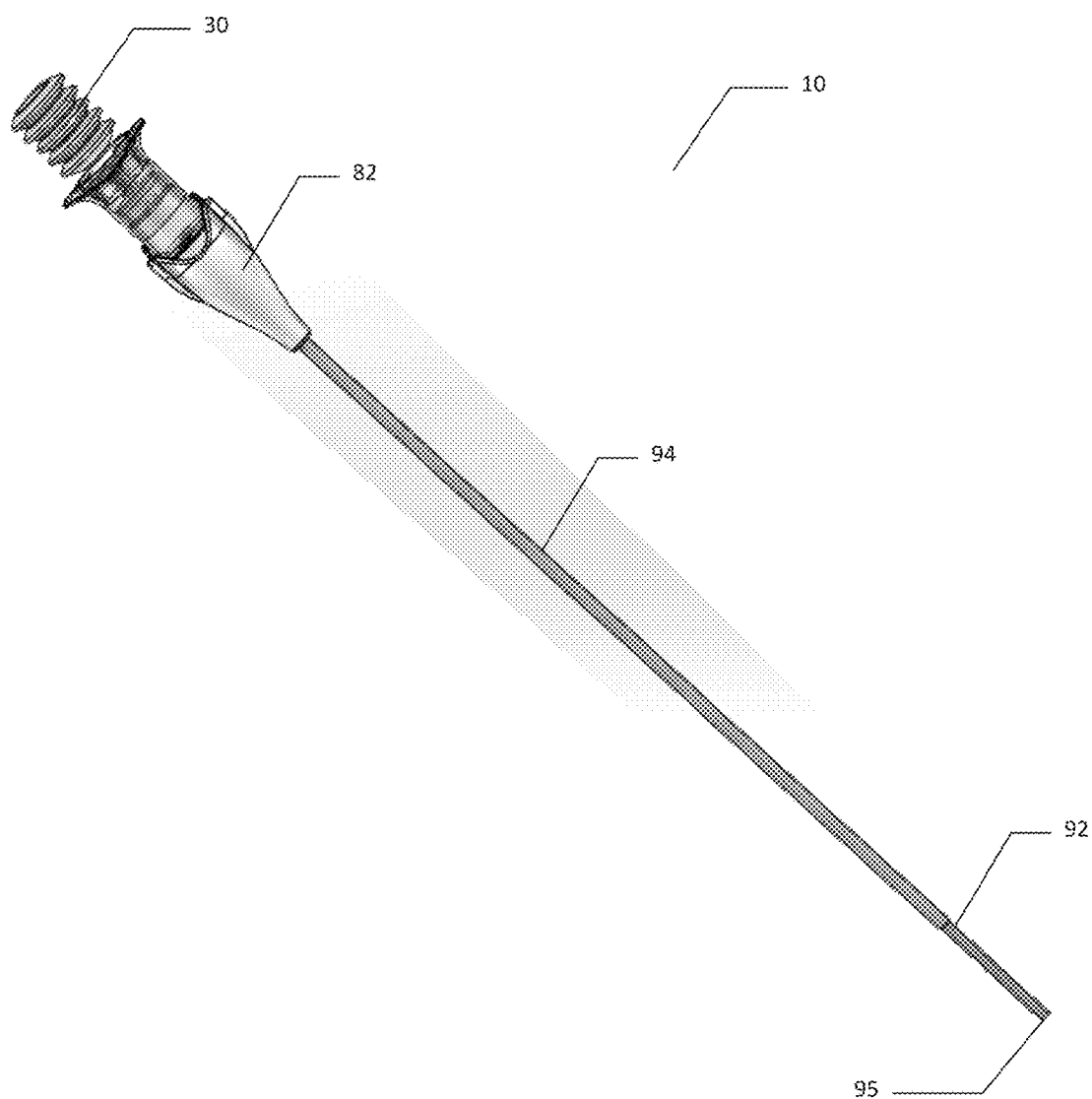
FIG. 20 shows an embodiment of the powder delivery device of the present invention with elongated cannula and rigid shaft with a shroud attached.

Further referring to FIG. 15, which shows schematically a partial cross-sectional view of device 10, as shown in FIG. 15A, upon applying pressure in the direction schematically shown by arrow 33 on bellows top 32, bellows 30 compresses generating air pressure inside bellows 30. Air is then moving through device 10 as schematically indicated by arrows 100 from bellows 30 via gap 41 and through filter 50 into powder compartment 22. From powder compartment 22, powder 110 and air stream are expressed from the device via cannula 90 (not shown in FIG. 15).

Upon release of pressure on bellows 30, bellows 30 returns to uncompressed state, creating a vacuum inside bellows 30. Air or gas is inspired into bellows 30, with air entering device 10 via cannula 90, passing through powder compartment 22, and filter 50. Filter 50 prevents powder penetration into bellows 30 so that bellows 30 is substantially free of powder throughout the expression.

Powder compartment 22 is maintained so that the volume of powder compartment 22 is substantially filled with powder, with substantially no free air space or minimal free air space. The inventors surprisingly discovered that such arrangement results in better uniformity of powder expression throughout the expression cycle, i.e. from when device 10 is fully charged with powder to emptying of powder compartment 22 of all remaining powder, as well as in better directional expressing uniformity, i.e. in minimal differences between the expression of powder with cannula 90 directed horizontally relative to directed vertically. Powder compartment is also maintained under low compression or no compression. The inventors surprisingly discovered that such arrangement results in much better uniformity of powder expression and prevents aggregation and agglomeration of powder.

Spring 45 serves as a compressible advancer of plunger 40 and filter 50. As bellows 30 is depressed, bellows 30 generates flow of air expressing powder from device 10. Simultaneously, top of bellows 32 is compressing spring 45, which in turn applies pressure on plunger 40 and filter 50 causing plunger 40 and filter 50 to move in distal direction, decreasing the volume of powder compartment 22 as powder is expressed from device 10.

Thus with each depression of bellows 30 generating air flow and powder expression from powder compartment 22, plunger 40 with filter 50 are simultaneously driven towards distal end 12 by spring 40 which is depressed upon compression of bellows 30. Thus upon each expression of powder from device 10, plunger 40 with filter 50, advances distally to take up the space freed by expressed powder. This action results in volume of powder compartment 22 being constantly adjusted to correspond to the volume of powder remaining in powder compartment 22.

Advantageously, upon release of bellows 30 pressure on spring 45 is released and spring can expand rearward or proximally freely, without pulling on plunger 40 with filter 50. Advantageously, spring 40 is not attached to bellows 30, resulting in spring 40 not being pulled proximally upon release of pressure on bellows 30 and expansion of bellows 30 into uncompressed state. Advantageously, plunger 40 with filter 50 are snugly and slidably fit inside reservoir 20 and remain in position furthest advanced during powder expression. During the inspiration of air into bellows, when pressure on bellows 30 is removed allowing bellows to expand, plunger 40 with filter 50 are not moving in proximal direction, instead maintaining the closest position to distal end 12 achieved during the prior powder expression cycle. The frictional engagement of plunger 40 with filter 50 against reservoir 20 prevents easy movement of plunger 40 with filter 50 rearward, i.e. in proximal direction.

Depression of bellows 30 results in simultaneous generation of gas pressure within device 10 and pressure on spring 45 which in turn forces plunger 40 with filter 50 advance within powder compartment 22 to take up any space freed by powder 110 expressed from powder compartment 22.

Advantageously, prior to any expression, there is no or very little pressure on powder in powder compartment 22. Because there is no or very little constant pressure of spring 45 on powder in powder compartment 22, potential agglomeration and caking of powder are prevented.

Referring to FIG. 15A, spring 45 is shown positioned on plunger stem 42. Spring 45 is situated between top of bellows 32 and plunger 40, and is shown touching top of bellows 32. Alternatively, as shown in FIG. 15B, spring 45 can end at a distance 46 from top of bellows 32, distance 46 ranging from 0 mm to about 20 mm, such as 3 mm, 5 mm, 7 mm, 15 mm. FIG. 15B can represent an initial position of spring 45, prior to any expression of powder 110.

FIG. 15B also shows position of spring 45, plunger 40 with filter 50, and powder compartment 22 after one or more powder 110 expressions. As shown in FIG. 15B, upon expression of powder 110 from powder compartment 22, volume of powder compartment 22 decreases with plunger 40 with filter 50 advancing within reservoir 20 and taking freed space. As shown, spring 45 is positioned at distance 46 from top of bellows 32, with distance 46 increasing after each expression.

Referring to FIGS. 16A and 16B, an alternative embodiment of the present invention is shown, in a view similar to the view shown in FIGS. 15A and 15B, whereby spring 45 and optionally plunger 40 are made of compressible foam.

Cannula 90 shown in FIGS. 1-9 is a tubular powder expression member, made of polymer or metal, and can be flexible, semi-flexible, bendable, or rigid. Cannula can have any cross-section, but is preferably tubular with internal diameter from 1 mm to 10 mm, such as 2 mm, 3 mm, 4 mm, 5 mm. Cannula 90 is preferably flexible and can have the length from 3 cm to about 50 cm, such as 4 cm, 5 cm, 10 cm, 20 cm, 30 cm, 40 cm.

Referring to FIG. 17, an elongated cannula 92 useful for laparoscopic applications is shown attached to device 10 at hub 80.

Referring to FIG. 18, a hollow tubular rigid shaft 94 attached to shroud 82 is shown. Rigid shaft 94 is utilized to be positioned over elongated cannula 92 to maintain elongated cannula 92 in a straight linear configuration for delivery through laparoscopic ports and trocars. Rigid shaft 94 has internal diameter closely matching or slightly larger than external diameter of elongated cannula 92, for easy insertion of elongated cannula 92 into rigid shaft 94. FIG. 19 shows insertion of elongated cannula 92 with hub 80 into rigid shaft 94 attached to shroud 82. Shroud 82 is attachable (such as by snap-on means) onto hub 80 and/or onto powder trap 70 and/or onto reservoir 20. FIG. 20 shows device 10 with shroud 82 and rigid shaft 94 attached, with elongated cannula 92 installed and visibly protruding from rigid shaft 94. The length of elongated cannula 92 is selected so as to extend from about 0 mm to about 30 mm from rigid shaft 94, such as extend by 1 mm, 5 mm, 20 mm.

In operation, device 10 filled with powder is brought into a sterile field in operating room. Device 10, if equipped with blocking feature, is then unblocked by aligning reservoir ridges 24 and powder trap ridges 75. Prior to unblocking, or after unblocking, device is directed at the wound or tissue that requires application of hemostatic powder, optionally through a laparoscopic port. Bellows 30 is then depressed, releasing a first portion of hemostatic powder. Bellows 30 is then released, allowing inspiration of air into bellows 30. Steps of depressing and releasing of bellows 30 are then continued sequentially as needed, expressing hemostatic powder towards tissue as needed.

In the device operation, there a number of ways a health practitioner can hold the device for delivering the hemostatic powder. In one application technique, the device 10 is held with one hand, gripping reservoir 20 between index finder and middle finger, or between middle finger and ring finger, and pressing on bellows 30 with the thumb of the same hand for powder expression.

In an alternative application technique, the device 10 is held with one hand, gripping reservoir 20 in a fist by wrapping one or more or index finder, middle finger, ring finger, and little finger, and pressing on bellows 30 with the thumb of the same hand for powder expression. Alternatively, device 10 can be held as convenient by one hand anywhere on reservoir 20, and the bellows 30 can be depressed by another hand. Many other convenient techniques of holding device 10 and depressing bellows 30 for expression of hemostatic powder are possible.

Figure 21:
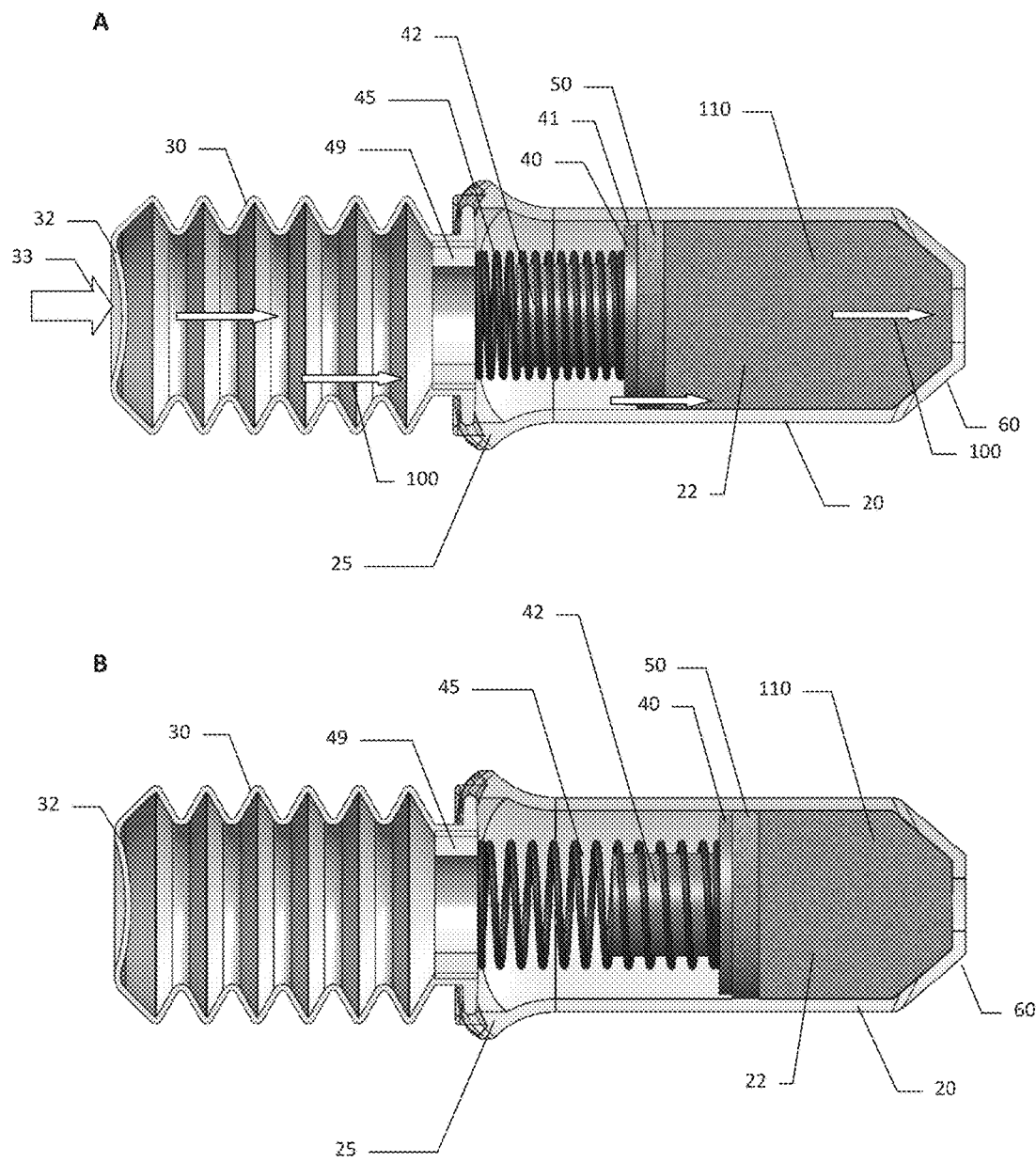

FIG. 21 shows an embodiment of device 10 whereby spring 45 is mounted onto plunger stem 42 between plunger 40 and flange 49. Spring 45 is under constant compression and constantly exerts pressure onto plunger 40. As shown in FIGS. 21A and 21B, upon depressing bellows 30, air moves through the device in a similar way as described above, resulting in expression of powder 110 from powder compartment 22. Pressure from spring 45 forces plunger 40 with filter 50 advances within powder compartment 22 to take up any space freed by powder 110 expressed from powder compartment 22.

FIG. 21B shows position of spring 45, plunger 40 with filter 50, and powder compartment 22 after one or more powder 110 expressions. Upon expression of powder 110 from powder compartment 22, volume of powder compartment 22 decreases with plunger 40 with filter 50 advancing within reservoir 20 and taking freed space. As shown, spring 45 has expanded and takes all space between flange 49 and plunger 40.

Figure 22:
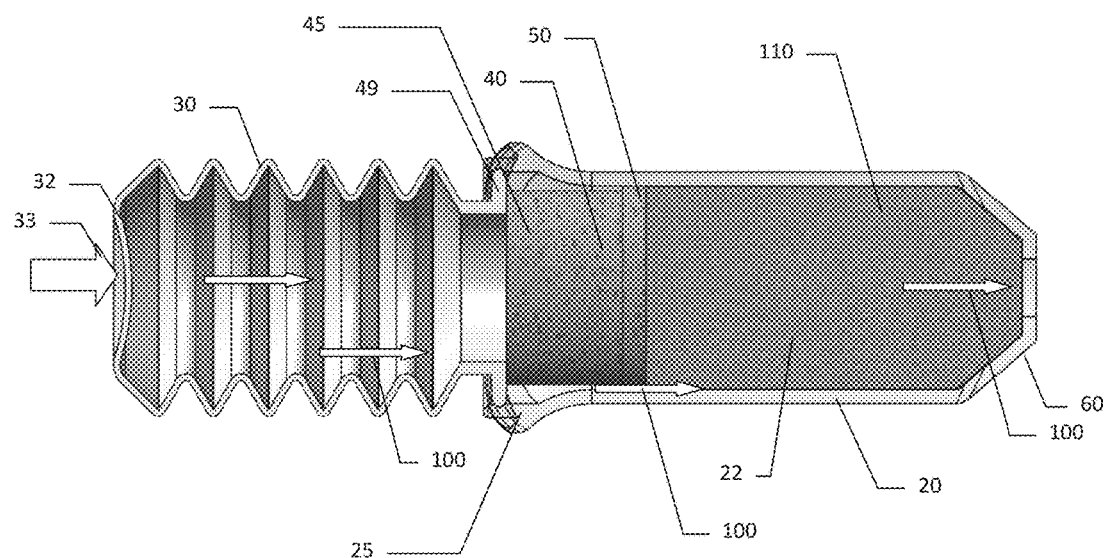
Figure 22:
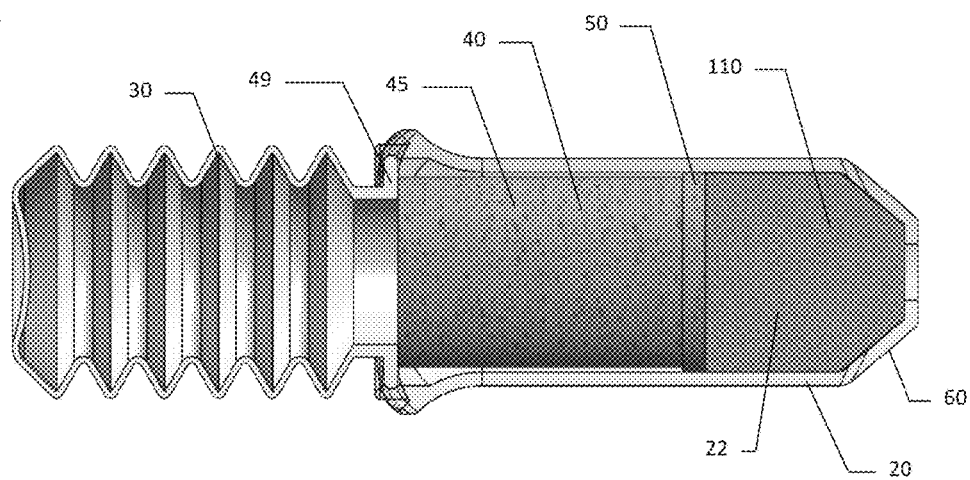

FIG. 22 shows an alternative embodiment of the present invention, in a view similar to the view shown in FIGS. 21A and 21B, whereby spring 45 and optionally plunger 40 are made of compressible foam.

Figure 23:
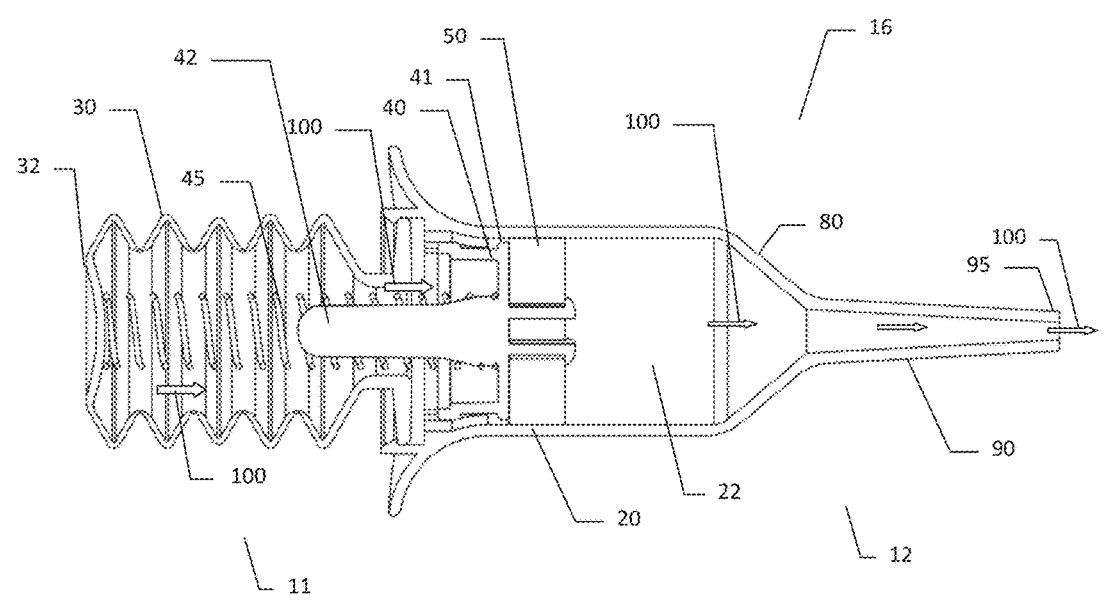

FIG. 23 shows an embodiment of inventive device 16 having, no optional powder trap 70, no optional tortuous path 72; no optional orifice 73; no optional reservoir ridges 24 and powder trap ridges 75; no optional blocking feature providing for blocking orifice 73; no optional blocking member 28. Device 16 operates in a similar way to embodiments shown in FIGS. 1-20, whereby upon depressing bellows 30, air moves through the device in a similar way as described above, resulting in expression of powder 110 from powder compartment 22. Pressure from spring 45 forces plunger 40 with filter 50 to advance within powder compartment 22 to take up any space freed by powder 110 expressed from powder compartment 22.

Reservoir 20 can be of any cross-sectional shape, such as rectangular or oval, and is preferably of circular cross-sectional shape, with internal cross-sectional diameter ranging from about 8 mm to about 40 mm, such as 10 mm, 15 mm, 20 mm, 21 mm, 25 mm, and 30 mm.

Figure 1:
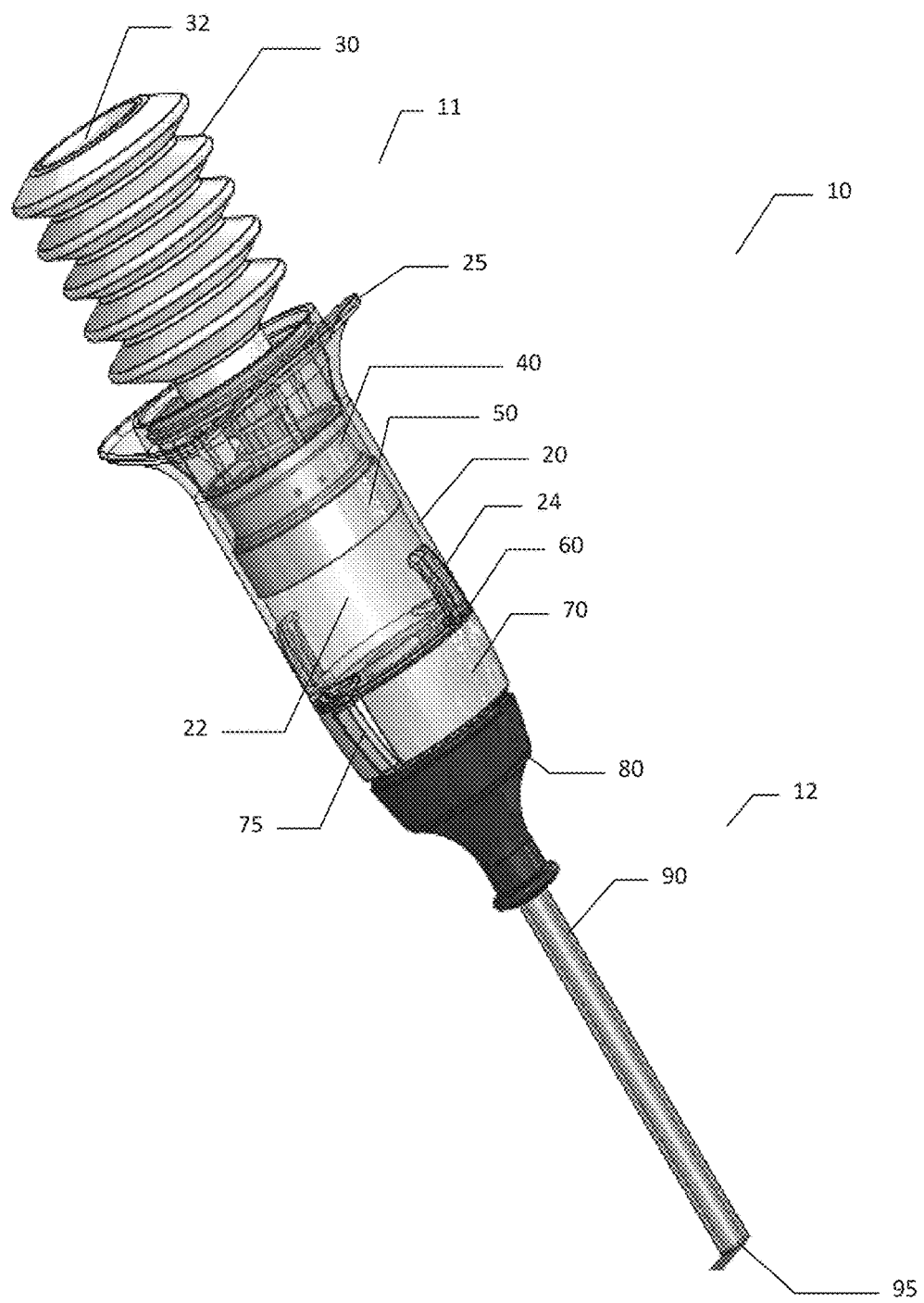
FIG. 1 shows an embodiment of the powder delivery device of the present invention in closed configuration.
Figure 2:
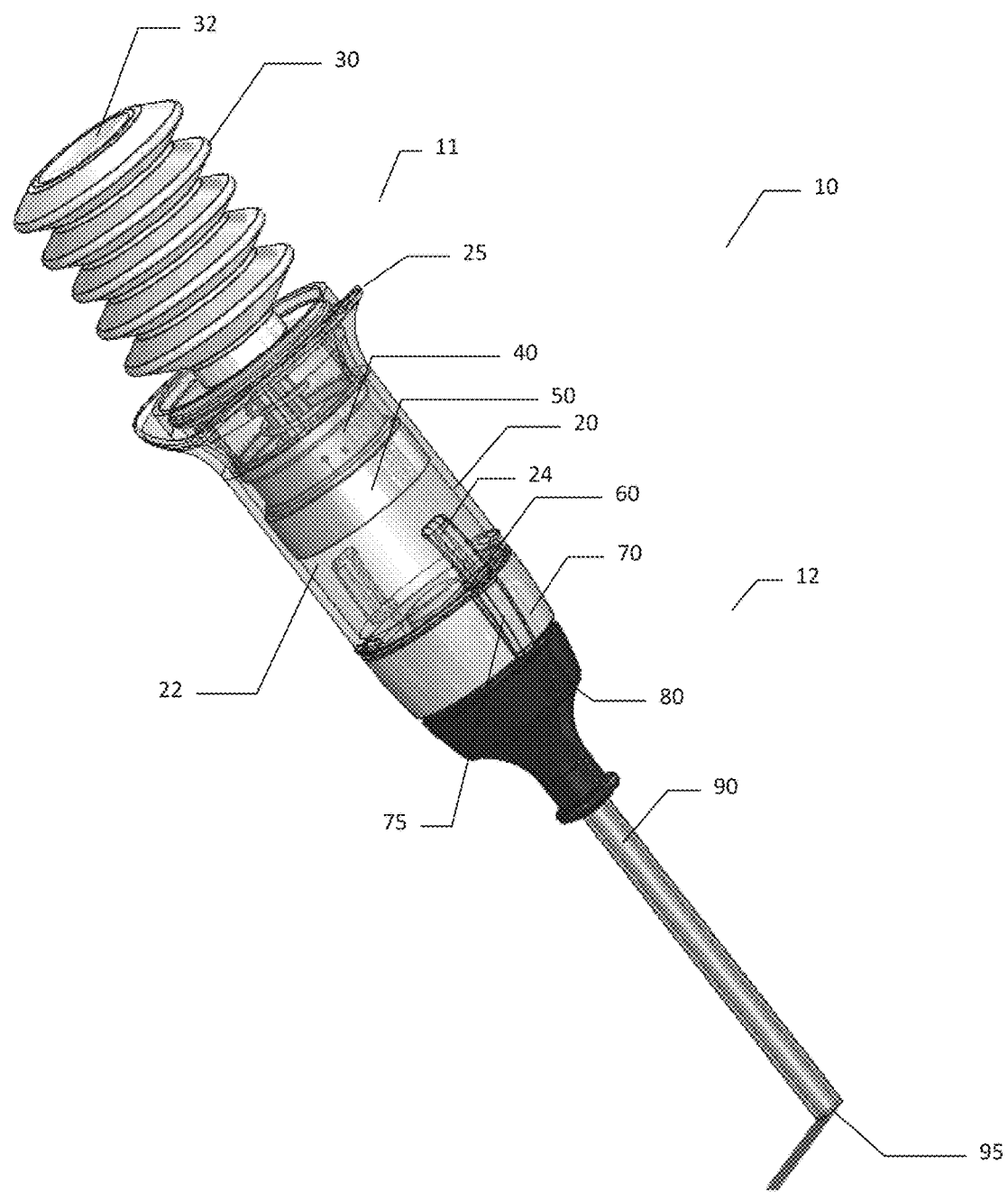
FIG. 2 shows an embodiment of the powder delivery device of the present invention in open configuration.
Figure 3:
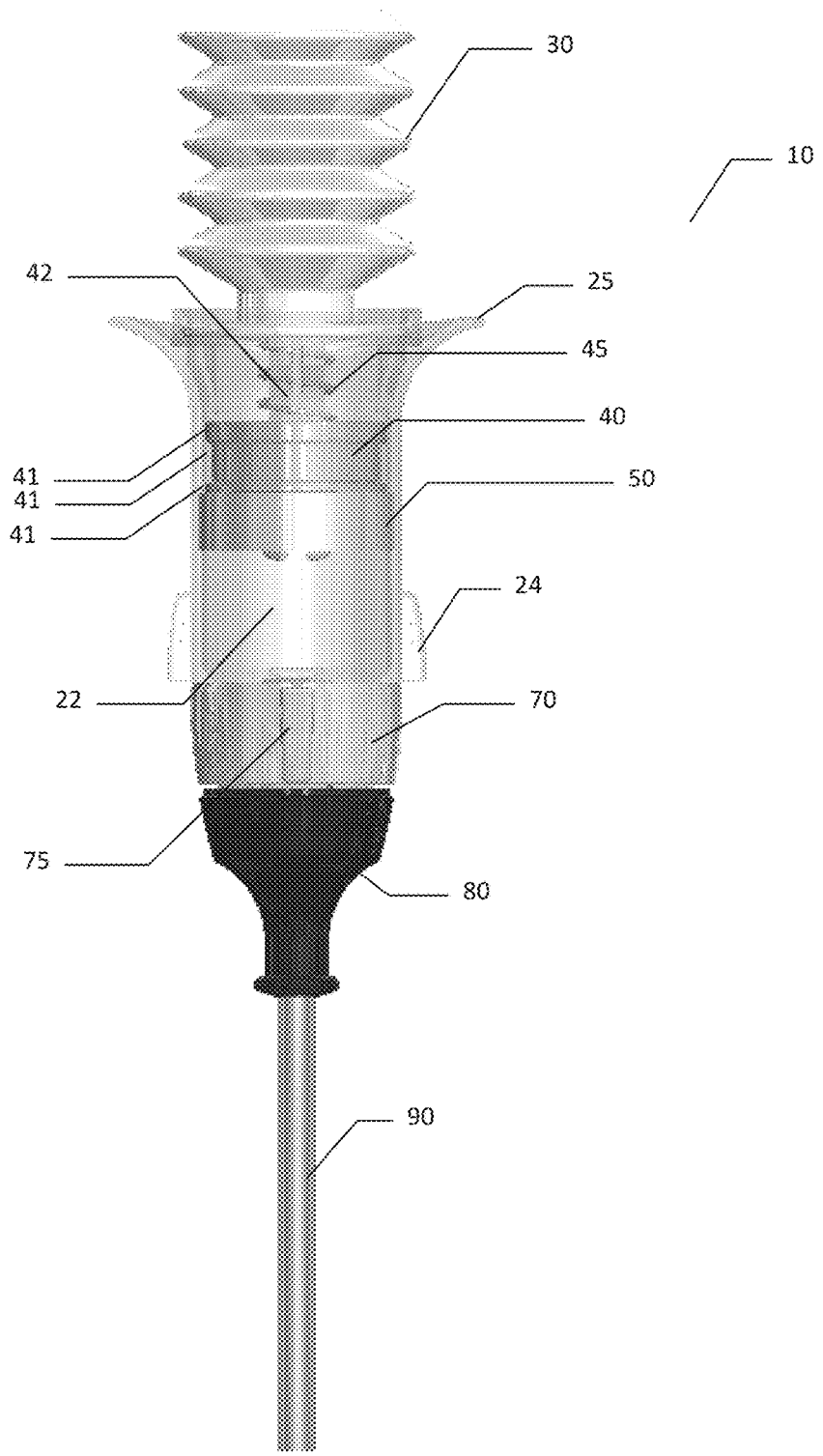
FIG. 3 shows an embodiment of the powder delivery device of the present invention in closed configuration.
Figure 4:
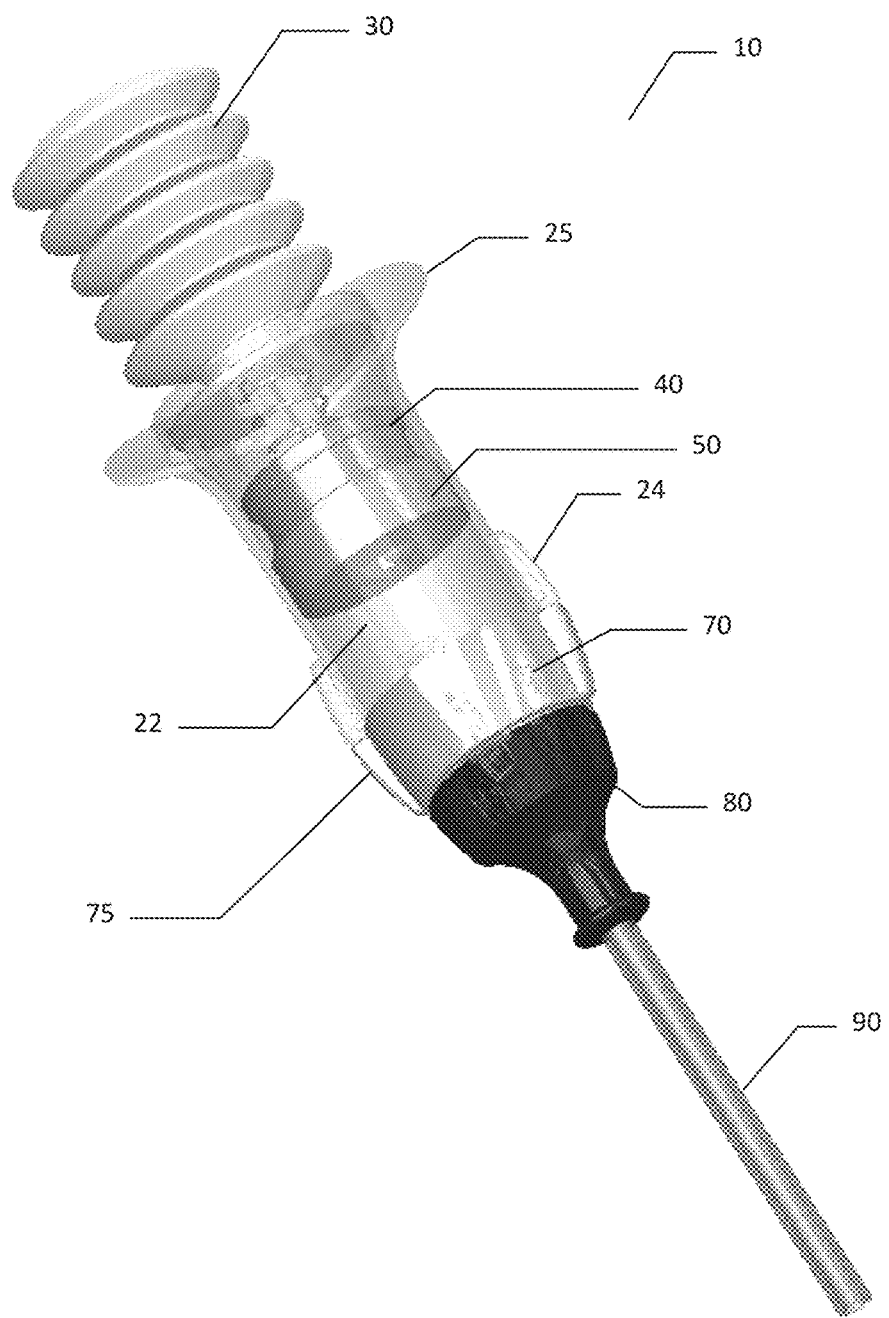
FIG. 4 shows an embodiment of the powder delivery device of the present invention in open configuration.

Bellows 30 has generally a tubular shape and is made of resilient polymeric material, such as polyethylene or polypropylene that enables bellows 30 to be compressed by applying pressure on top of bellows 32, so that when the pressure is removed bellows 30 returns to substantially the same shape as before the compression was applied. Bellows 30 is compressible from about 2:1 ratio of initial height to compressed height to about 6:1 ratio, such as 3:1 ratio of initial height to compressed height. In one embodiment, bellows 30 is about 22 mm in diameter, about 30 mm in uncompressed state, and about 10 mm in fully compressed state, having from 3 to 10 hinges, such as 5 hinges as shown in FIG. 1.

Microporous filter 50 can be made of any porous media such as micro-porated or sintered polymeric material, e.g. PTFE, polyethylene, polypropylene, or similar, preferably with interconnected pores or channels to selectively allow gas flow through filter 50 while preventing flow of powder through filter 50. Pore size or channel density are selected to selectively block passage of powder particles being used, for instance particles ranging from 0.001 mm to 1.0 mm in size, more preferably from 0.05 mm to 0.5 mm, such as particles with effective diameter of 0.05 mm, 0.1 mm, 0.15 mm, 0.20 mm, 0.25 mm, 0.3 mm, 0.35 mm, 0.5 mm. In one embodiment, pore size is at least 20% lower than the average size of particles of the hemostatic powder, such as 50% lower. In the preferred embodiment, filter 50 will block passage of particles with size greater than 0.05 mm.

Spring 45 can be any spring of known types, such as metal wire based spring, or polymeric string based spring. Alternatively, spring 45 is made of compressible and resilient foam.

Filling device 10 with an appropriate hemostatic powder can be performed in a variety of ways. In one method of filling device 10, device 10 is prepared for filling with bellows 30, plunger 40, filter 50, spring 45 removed from reservoir 20, while powder trap 70 is mounted onto port 60, with orifice 73 blocked by blocking member 28 within reservoir 20 and thus closing orifice 73 and preventing powder entering tortuous path 72. Reservoir 20 is then oriented with proximal end 11 facing generally upwards, and reservoir 20 is filled by hemostatic powder gravimetrically or volumetrically through open proximal end 11. In one embodiment, device 10 is filled with 2-10 g of hemostatic powder, such as 3 g, 4 g, or 5 g of hemostatic powder by weight. Thereafter, maintaining vertical orientation of device 10 with proximal end 11 facing generally upwards, plunger 40 and filter 50 are inserted into reservoir 20 from proximal end 11. Thereafter spring 45 is mounted onto plunger stem 42 and bellows 30 is attached to reservoir 20 at proximal end 11.

Example 1

Powder Expression—Comparative

A comparative device that is commercially available as the Arista™ delivery device is available from Davol Inc., a subsidiary of C. R. Bard, Inc. The comparative device is pre-filled with 3 g of plant based absorbable surgical hemostatic powder derived from purified plant starch, with no modifications made to the commercially available comparative device or powder filling of said device. The comparative device used in the testing is shown schematically in FIG. 24. Comparative device 17 comprises bellows 30 mounted onto reservoir 20 with grip 25. Powder compartment 22 within reservoir 20 is pre-filled with the hemostatic powder. Device 13 had a tubular expression cannula 90 having a cannula exit 95.

Figure 24:
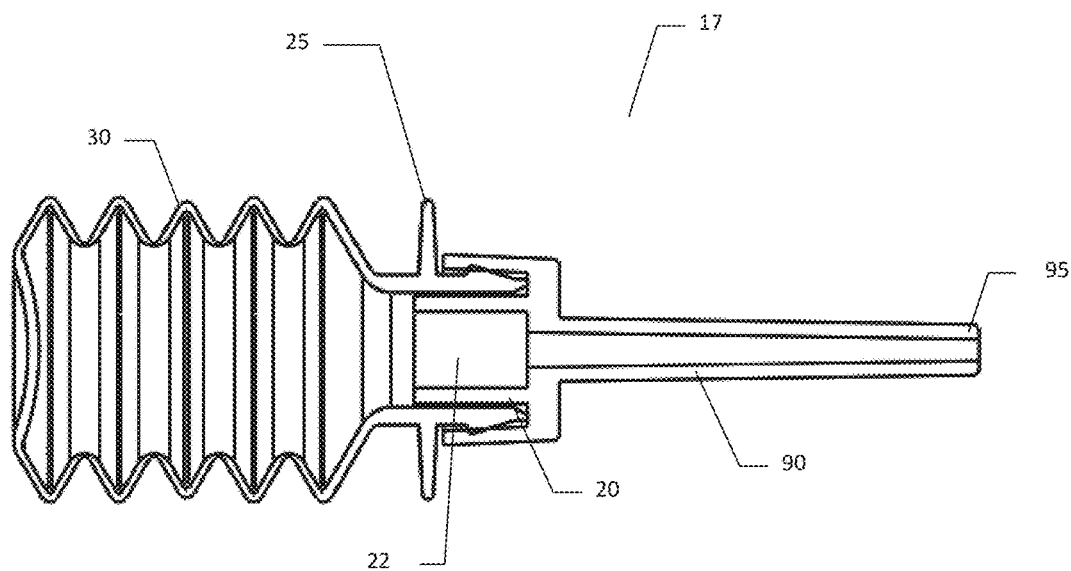
Figure 25:
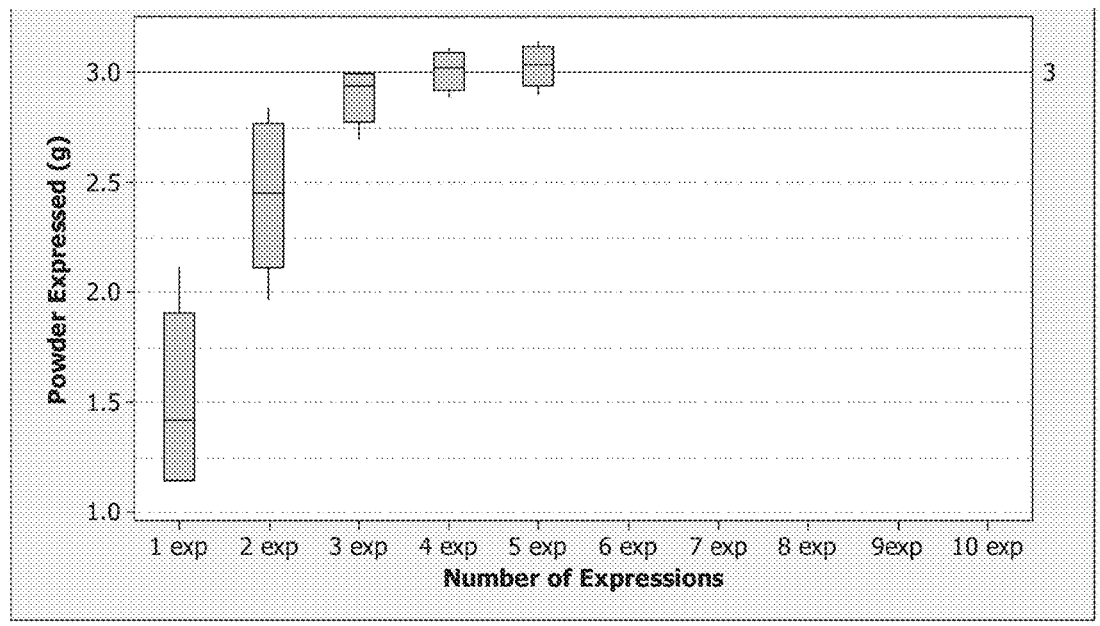

Referring to FIGS. 25 and 26, the results of powder expression testing using comparative device 17 are shown of FIG. 24. The powder was expressed in sequential expressions or bursts when the comparative device was oriented vertically (with cannula 90 and cannula exit 95 facing downwards) with the data presented in FIG. 25; or horizontally (with cannula 90 and cannula exit 95 facing horizontally) with the data presented in FIG. 26. The quantities of powder expressed with each expression or powder burst were measured and plotted as cumulative grams expressed vs. the sequential number of expression. As can be seen from FIG. 25, the comparative device shows highly non-uniform expression of hemostatic powder in vertical orientation, whereby only two expressions express almost all of the powder, and by the fourth expression all 3 g of powder are expressed. This expression pattern is highly non-uniform and inconvenient for the health practitioner, overloading first and second expressions and then expressing little or no powder. This expression pattern is also inconvenient for covering areas of tissue or wound as in only two expressions 80% of the hemostatic powder is expressed leaving nothing for adjacent areas of tissue. Overall in four expressions, all 3 grams of powder were expressed, i.e. on average about 0.75 g per expression was expressed, with first two expressions delivering on average about 1.25 g per expression.

As can be seen from FIG. 26, the comparative device shows non-uniform and incomplete expression of hemostatic powder also in horizontal orientation, whereby by seventh expression of powder the expression of powder ceases with only 2 g or 66% of powder expressed, and 33% of powder still remaining in the device. This expression pattern is inconvenient for the health practitioner, whereby the remaining powder ceases to be expressed from the device in horizontal orientation. On average, the device expressed about 0.25 g per expression, but also failed to express all powder.

Further, with health practitioner changing the direction of expression from horizontal to vertical or any angle in-between, the expression patterns will also change, resulting in unpredictable patterns and expressing more or less powder than expected or needed in each expression. For instance, as shown above, changing orientation can result in changes from 1.25 g per expression to 0.25 g per expression.

Example 2

Powder Expression

The hemostatic powder used in testing of the devices of present invention was made from oxidized regenerated cellulose by milling and roller compaction. Briefly, SURGICEL™ ORC fabric was subject to milling and roller compaction. The resulting powder target size was 75 µm-300 µm.

Referring to FIGS. 27 and 28, the results of powder expression testing in the inventive device are shown. Device 10 was loaded with 3 g of hemostatic ORC powder as described above, and the powder was expressed in sequential expressions or powder bursts when device 10 was oriented vertically (with cannula 90 and cannula exit 95 facing downwards), with the data presented in FIG. 27; or horizontally (with cannula 90 and cannula exit 95 facing horizontally), with the data presented in FIG. 28). The quantities of powder expressed with each 5 expressions or powder bursts were measured and plotted as cumulative grams expressed vs. the number of expression. As can be seen from FIG. 27, device 10 shows highly uniform expression of hemostatic powder in vertical orientation, whereby all 3 g of hemostatic powder are expressed in about 35 uniform expressions (grouped in FIG. 27 by five expressions). This expression pattern is uniform and convenient for the health practitioner, resulting in predictable hemostatic powder delivery and delivering smaller quantities of powder, i.e. about 0.075-0.10 g of powder per expression, such as 0.085 g of powder per expression.

As can be seen from FIG. 28, device 10 shows highly uniform expression of hemostatic powder in horizontal orientation as well, whereby all 3 g of hemostatic powder are expressed in seven uniform expressions, albeit with the seventh expression being somewhat lower than previous six. This expression pattern, similarly to data in FIG. 27, is uniform and convenient for the health practitioner, resulting in a predictable hemostatic powder delivery and delivering smaller quantities of powder, i.e. about 0.075-0.10 g of powder per expression, such as 0.085 g of powder per expression.

Further, with health practitioner changing the direction of expression from horizontal to vertical or any angle in-between, the expression patterns will remain substantially unchanged, resulting in predictable patterns and expressing approximately same amount of powder in each expression independently of the orientation of device 10. Device 10 demonstrates substantial independence of the expression of powder from orientation, with orientation changing from downward vertical to horizontal. Further, device 10 demonstrates per expression quantities at the beginning of the powder delivery, i.e. when device 10 is 90-100% full with powder, very similar to per expression quantities at the end of the powder delivery, i.e. when device 10 is almost emptied of the powder, or has 5%-15% powder remaining. Per expression quantities at the beginning of the powder delivery are preferably varying by not more than 5% to 25%, such as varying by not more than 5%, 10%, or 20%.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. The scope of the present invention should be considered in terms of the following claims and is understood not to be limited to the details of structure and operation shown and described in the specification and drawings.

We claim:

1. A device for expression of a powder, comprising:

a) an elongated hollow reservoir, the reservoir having a manual air pump attached to the reservoir and an open-ended port at a distal end of said reservoir, b) a porous filter slidably disposed within the reservoir between said manual air pump and said open-ended port;

c) a spring disposed within the reservoir between the air pump and the porous filter;

wherein the powder is disposed within the reservoir between the porous filter and the open-ended port, and the manual air pump is in a fluid communication with the open-ended port through the porous filter and through the powder, wherein said porous filter comprises interconnected pores or channels having size preventing the powder from passing through the porous filter and preventing said powder from penetration into said air pump whereby said air pump is free of said powder, wherein said device provides repeated compression and release of the manual air pump for the repeated expression of a quantity of said powder, and whereby said device delivers uniform quantities of said powder expressed over a plurality of sequential expressions, wherein said spring, when compressed, applies pressure on said porous filter causing said filter to move in the distal direction, wherein said manual air pump comprises a bellows.

2. The device of claim 1, wherein said porous filter is attached to a plunger slidably disposed within the reservoir between said porous filter and said manual air pump and a hollow expression cannula is attached to said open-ended port and extends from the device distally, said expression cannula is in fluid communication with said manual air pump.

3. The device of claim 2, wherein said plunger has an elongated stem extending from said plunger towards the proximal end and said spring is at least partially supported on said stem.

4. The device of claim 2, further comprising
   a) a powder trap positioned between the open-ended port and the expression cannula, the powder trap comprising
      i) a tortuous channel for the powder, the channel having an entrance orifice open to the reservoir and an exit opening open to the expression cannula.

5. The device of claim 4, further comprising a blocking member within the reservoir, wherein said powder trap is rotatable about the reservoir from a first position to a second position and in the first position the entrance orifice is blocked by the blocking member and in the second position the entrance orifice is not blocked by the blocking member.

6. The device of claim 4, wherein the manual air pump is in the fluid communication with the expression cannula through the reservoir, the plunger, the porous filter, the powder, the entrance orifice, the tortuous channel, and the exit opening.

7. The device of claim 4, further comprising a gap between the plunger and a wall of the reservoir.

8. The device of claim 4, wherein the plunger has at least one aperture establishing the fluid communication between the manual air pump and the porous filter.

9. The device of claim 4, wherein the spring is in a non-compressed state prior to expressing the powder.

10. The device of claim 4, wherein the spring is compressed towards the distal end by compressing the manual air pump.

11. The device of claim 1, wherein said powder is a hemostatic powder.

12. The device of claim 1, wherein said powder is an ORC powder.

13. The device of claim 1, wherein a quantity of the powder expressed from the device is independent of the device orientation.

14. The device of claim 1, wherein a quantity of the powder expressed from the device by each individual expression at the beginning of the powder delivery is varying by not more than 10 percent from the quantity of the powder expressed from the device by each individual expression at the end of the powder delivery.

15. A method for expressing a hemostatic powder comprising the steps of:
   a) directing the open-ended port of the device of claim 1 towards a target;
   b) compressing the manual air pump thus supplying pressurized air into the reservoir and simultaneously compressing the spring thus exerting pressure on the porous filter;
   c) allowing the pressurized air to reach the powder through the porous filter and to exit the device from the open-ended port with a portion of the powder;
   d) simultaneously advancing the porous filter towards the distal end under pressure from the spring, thus keeping the powder compressed under the porous filter;
   e) releasing the manual air pump allowing ambient air to refill the air pump;
   f) optionally repeating the steps (b) through (e).

16. The device of claim 1, said device wherein, upon compression of said manual air pump, pressurized air moves through said porous filter into said reservoir; and, upon release of said air pump, ambient air is drawn into said manual air pump that passes through said porous filter to refill said air pump.

17. The device of claim 1, wherein said porous filter advances within the reservoir upon each expression of a quantity of said powder.

* * * * *